(12) United States Patent
Rostami et al.

(10) Patent No.: US 6,337,051 B1
(45) Date of Patent: Jan. 8, 2002

(54) DEVICE FOR DETECTING FORMATION OF A SECOND LIQUID PHASE

(75) Inventors: Ader M. Rostami, Bainbridge Island; David C. DeCoster, Buckley, both of WA (US); Eustathios Vassiliou, Newark, DE (US); Mark W. Dassel, Indianola; Sharon M. Aldrich, Poulsbo, both of WA (US)

(73) Assignee: RPC Inc., Atlanta, GA (US)

( * ) Notice: Subject to any disclaimer, the term of this patent is extended or adjusted under 35 U.S.C. 154(b) by 0 days.

(21) Appl. No.: 08/876,692

(22) Filed: Jun. 16, 1997

Related U.S. Application Data

(63) Continuation-in-part of application No. 08/812,847, filed on Mar. 6, 1997, and a continuation-in-part of application No. 08/824,992, filed on Mar. 27, 1997, now Pat. No. 5,922,908.
(60) Provisional application No. 60/020,798, filed on Jun. 24, 1996.

(51) Int. Cl.$^7$ ........................... B32B 5/18; G01N 21/29; G01N 27/02; G01N 27/00
(52) U.S. Cl. ................ 422/76.78; 422/82.05; 422/62; 422/76; 422/82.01; 422/82.02
(58) Field of Search ................ 422/76, 78, 82.05, 422/62, 82.01, 82.02

(56) References Cited

U.S. PATENT DOCUMENTS

| | | | |
|---|---|---|---|
| 1,121,532 A | 12/1914 | Newberry | 23/299 |
| 2,014,044 A | 9/1935 | Haswell | 75/17 |
| 2,223,493 A | 12/1940 | Loder | 260/537 |
| 2,223,494 A | 12/1940 | Loder | 260/586 |
| 2,301,240 A | 11/1942 | Baumann et al. | 183/115 |
| 2,439,513 A | 4/1948 | Hamblet et al. | 260/533 |
| 2,557,282 A | 6/1951 | Hamblet et al. | 260/533 |
| 2,565,087 A | 8/1951 | Porter et al. | 260/631 |
| 2,980,523 A | 4/1961 | Dille et al. | 48/215 |
| 3,161,603 A | 12/1964 | Leyson et al. | 252/413 |
| 3,231,608 A | 1/1966 | Kollar | 260/533 |
| 3,234,271 A | 2/1966 | Barker et al. | 260/531 |
| 3,290,369 A | 12/1966 | Bonfield et al. | 260/537 |
| 3,361,806 A | 1/1968 | Lidov | 260/531 |
| 3,515,751 A | 6/1970 | Oberster et al. | 260/533 |
| 3,530,185 A | 9/1970 | Pugi | 260/586 |
| 3,613,333 A | 10/1971 | Gardenier | 55/89 |
| 3,677,696 A | 7/1972 | Bryk et al. | 23/2 |
| 3,791,195 A | * 2/1974 | Loe | 73/27 R |
| 3,928,005 A | 12/1975 | Laslo | 55/73 |
| 3,932,513 A | 1/1976 | Russell | 260/586 |
| 3,946,076 A | 3/1976 | Paasen et al. | 260/586 |
| 3,957,876 A | 5/1976 | Rapoport et al. | 260/586 |
| 3,987,100 A | 10/1976 | Barnette et al. | 260/586 |
| 3,987,808 A | * 10/1976 | Carbonell et al. | 137/3 |
| 4,032,569 A | 6/1977 | Onopchenko et al. | 260/533 C |
| 4,039,304 A | 8/1977 | Bechthold et al. | 55/10 |
| 4,055,600 A | 10/1977 | Langley et al. | 260/586 |
| 4,065,527 A | 12/1977 | Graber | 261/79 A |
| 4,158,739 A | 6/1979 | Schulz et al. | 562/543 |
| 4,263,453 A | 4/1981 | Schulz et al. | 562/543 |
| 4,308,037 A | 12/1981 | Meissner et al. | 55/10 |
| 4,325,910 A | * 4/1982 | Jordan | 422/64 |
| 4,361,965 A | 12/1982 | Goumondy et al. | 34/57 |

(List continued on next page.)

FOREIGN PATENT DOCUMENTS

| | | | |
|---|---|---|---|
| DE | 4426132 A1 | 1/1996 | C07C/53/08 |
| DE | 4427474 A1 | 2/1996 | |
| EP | 439 007 A2 | 7/1991 | C07C/63/38 |
| EP | 751 105 A2 | 1/1997 | C07B/33/00 |
| FR | 2 722 783 A1 | 1/1996 | C07C/55/14 |
| GB | 415172 | 8/1934 | |
| GB | 738808 | 10/1955 | |
| GB | 1143213 | 2/1969 | 51/16 |
| JP | 48-003815 | 2/1973 | |
| WO | WO96/03365 | 2/1996 | C07C/55/14 |
| WO | WO 96/40610 | 12/1996 | C07C/51/16 |

OTHER PUBLICATIONS

E. Sorribes et al., "Formación de neuvas fases en el proceso de obtención de ácido adípico: causas y efectos que provocan," *Rev. R. Acad. Cienc. Exactas, Fis. Nat. Madrid* (1987), 81 (1), 233–5 (+English language translation).

U.S. application No. 08/587967, Mark Dassel et al., filed Jan. 17, 1996.

U.S. application No. 08/812847, Dassel et al., filed Mar. 6, 1997.

U.S. application No. 08/859,985, Vassiliou et al., filed May 21, 1997.

U.S. application No. 08/861,281, Dassel et al., filed May 21, 1997.

U.S. application No. 08/861,180, DeCoster et al., filed May 21, 1997.

U.S. application No. 08/861,176, Dassel et al., filed May 21, 1997.

U.S. application No. 08/859,890, Rostami et al., filed May 21, 1997.

U.S. application No. 08/861,210, Vassiliou et al., filed May 21, 1997.

U.S. application No. 08/824,992, Dassel et al., filed Mar. 27, 1997.

U.S. application No. 08/477,195, Dassel et al., filed Jun. 7, 1995.

*Primary Examiner*—Alan Siegel
(74) *Attorney, Agent, or Firm*—Seed Intellectual Property Law Group PLLC

(57) ABSTRACT

This invention relates to monitors used in the oxidation of hydrocarbons to respective acids, which monitors are capable to detect formation of a second liquid phase in the reaction mixture. The reactions are conducted in a single liquid phase, and formation of a second liquid phase is highly undesirable. The information gathered by the detector is provided to a controller, which controller in turn takes measures to re-establish operation of the reaction in a single liquid phase.

25 Claims, 5 Drawing Sheets

U.S. PATENT DOCUMENTS

| | | | |
|---|---|---|---|
| 4,370,304 A | 1/1983 | Hendriks et al. | 422/224 |
| 4,394,139 A | 7/1983 | Board | 55/20 |
| 4,419,184 A | 12/1983 | Backlund | 162/49 |
| 4,423,018 A | 12/1983 | Lester, Jr. et al. | 423/243 |
| 4,695,430 A * | 9/1987 | Coville et al. | 422/65 |
| 4,749,657 A * | 6/1988 | Takahashi et al. | 436/146 |
| 4,989,452 A * | 2/1991 | Toon et al. | 73/293 |
| 5,061,453 A | 10/1991 | Krippl et al. | 422/106 |
| 5,104,492 A | 4/1992 | King et al. | 203/15 |
| 5,123,936 A | 6/1992 | Stone et al. | 55/8 |
| 5,170,727 A | 12/1992 | Nielsen | 110/346 |
| 5,206,701 A * | 4/1993 | Taylor et al. | 356/325 |
| 5,221,800 A | 6/1993 | Park et al. | 562/543 |
| 5,244,603 A | 9/1993 | Davis | 261/87 |
| 5,270,019 A | 12/1993 | Melton et al. | 422/234 |
| 5,271,904 A | 12/1993 | Esposito et al. | 422/105 |
| 5,286,458 A | 2/1994 | Yang et al. | 422/168 |
| 5,294,378 A | 3/1994 | Succi et al. | 261/130 |
| 5,312,567 A | 5/1994 | Kozma et al. | 261/87 |
| 5,321,157 A | 6/1994 | Kollar | 562/543 |
| 5,368,391 A * | 11/1994 | Crowe et al. | 374/10 |
| 5,374,767 A | 12/1994 | Drinkard et al. | 560/193 |
| 5,396,850 A | 3/1995 | Conochie et al. | 110/346 |
| 5,399,750 A | 3/1995 | Brun et al. | 562/553 |
| 5,463,119 A | 10/1995 | Kollar | 562/543 |
| 5,502,245 A | 3/1996 | Dassel et al. | 562/413 |
| 5,558,842 A | 9/1996 | Vassiliou et al. | 422/108 |
| 5,580,531 A | 12/1996 | Vassiliou et al. | 422/108 |
| 5,654,475 A | 8/1997 | Vassiliou et al. | 562/413 |
| 5,756,837 A | 5/1998 | Costantini et al. | 562/543 |

* cited by examiner

DEVICE FOR DETECTING FORMATION OF A SECOND LIQUID PHASE

CROSS-REFERENCES TO RELATED APPLICATIONS

This application is a continuation-in-part of U.S. patent application Ser. No. 08/812,847, filed on Mar. 6, 1997, which in turn claims priority of Provisional Application No. 60/020,798, filed on Jun. 24, 1996; and is a continuation-in-part of U.S. patent application Ser. No. 08/824,992, filed Mar. 27, 1997 now U.S. Pat. No. 5,922,908; all of which are incorporated herein by reference.

TECHNICAL FIELD

This invention relates to methods and devices for oxidizing hydrocarbons, such as cyclohexane for example, to respective acids, such as adipic acid for example, by a direct process.

BACKGROUND OF THE INVENTION

There is a plethora of references (both patents and literature articles) dealing with the formation of acids, one of the most important being adipic acid, by oxidation of hydrocarbons. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process", the "Boric Acid Process", and the "Direct Synthesis Process", which involves direct oxidation of cyclohexane to adipic acid with oxygen in the presence of solvents, catalysts, and promoters.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is well known that after a reaction has taken place according to the Direct Synthesis, a mixture of two liquid phases is present at ambient temperature, along with a solid phase mainly consisting of adipic acid. The two liquid phases have been called the "Polar Phase" and the "Non-Polar Phase." However, no attention has been paid so far to the importance of the two phases, except for separating the adipic acid from the "Polar Phase" and recycling these phases to the reactor partially or totally with or without further treatment.

It is also important to note that most studies on the Direct Synthesis have been conducted in a batch mode, literally or for all practical purposes.

There is a plethora of references dealing with oxidation of organic compounds to produce acids, such as, for example, adipic acid and/or intermediate products, such as for example cyclohexanone, cyclohexanol, cyclohexylhydroperoxide, etc.

The following references, among the plethora of others, may be considered as representative of oxidation processes relative to the preparation of diacids and intermediate products.

U.S. Pat. No. 5,463,119 (Kollar) discloses a process for the oxidative preparation of $C_5$–$C_8$ aliphatic dibasic acids by
 (1) reacting,
  (a) at least one saturated cycloaliphatic hydrocarbon having from 5 to 8 ring carbon atoms in the liquid phase and
  (b) an excess of oxygen gas or an oxygen-containing gas in the presence of
  (c) a solvent comprising an organic acid containing only primary and/or secondary hydrogen atoms and
  (d) at least about 0.002 mole per 1000 grams of reaction mixture of a polyvalent heavy metal catalyst;
 (2) removing the aliphatic dibasic acid; and
 (3) recycling intermediates, post oxidation components, and derivatives thereof remaining after removal of the aliphatic dibasic acid into the oxidation reaction.

U.S. Pat. No. 5,374,767 (Drinkard et al.) discloses formation of cyclohexyladipates in a staged reactor, e.g., a reactive distillation column. A mixture containing a major amount of benzene and a minor amount of cyclohexene is fed to the lower portion of the reaction zone and adipic acid is fed to the upper portion of the reaction zone, cyclohexyladipates are formed and removed from the lower portion of the reaction zone and benzene is removed from the upper portion of the reaction zone. The reaction zone also contains an acid catalyst.

U.S. Pat. No. 5,321,157 (Kollar) discloses a process for the preparation of $C_5$–$C_8$ aliphatic dibasic acids through oxidation of corresponding saturated cycloaliphatic hydrocarbons by
 (1) reacting, at a cycloaliphatic hydrocarbon conversion level of between about 7% and about 30%,
  (a) at least one saturated cycloaliphatic hydrocarbon having from 5 to 8 ring carbon atoms in the liquid phase and
  (b) an excess of oxygen gas or an oxygen containing gas mixture in the presence of
  (c) less than 1.5 moles of a solvent per mole of cycloaliphatic hydrocarbon (a), wherein said solvent comprises an organic acid containing only primary and/or secondary hydrogen atoms and
  (d) at least about 0.002 mole per 1000 grams of reaction mixture of a polyvalent heavy metal catalyst; and
 (2) isolating the C5–C8 aliphatic dibasic acid.

U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,932,513 (Russell) discloses the oxidation of cyclohexane with molecular oxygen in a series of reaction zones, with vaporization of cyclohexane from the last reactor effluent and parallel distribution of this cyclohexane vapor among the series of reaction zones.

U.S. Pat. No. 3,530,185 (Pugi) discloses a process for manufacturing precursors of adipic acid by oxidation with an oxygen-containing inert gas which process is conducted in at least three successive oxidation stages by passing a stream of liquid cyclohexane maintained at a temperature in the range of 140° to 200° C. and a pressure in the range of 50 to 350 p.s.i.g. through each successive oxidation stage and by introducing a mixture of gases containing oxygen in each oxidation stage in an amount such that substantially all of the oxygen introduced into each stage is consumed in that stage thereafter causing the residual inert gases to pass countercurrent into the stream of liquid during the passage of the stream through said stages.

U.S. Pat. No. 3,515,751 (Oberster et al.) discloses a process for the production of epsilon-hydroxycaproic acid in which cyclohexane is oxidized by liquid phase air oxidation in the presence of a catalytic amount of a lower aliphatic carboxylic acid and a catalytic amount of a peroxide under certain reaction conditions so that most of the oxidation products are found in a second, heavy liquid layer, and are directed to the production of epsilon-hydroxycaproic acid.

U.S. Pat. No. 3,361,806 (Lidov et al.) discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture.

U.S. Pat. No. 3,234,271 (Barker et al.) discloses a process for the production of adipic acid by the two-step oxidation of cyclohexane with oxygen. In a preferred embodiment, mixtures comprising cyclohexanone and cyclohexanol are oxidized. In another embodiment, the process involves the production of adipic acid from cyclohexane by oxidation thereof, separation of cyclohexane from the oxidation mixture and recycle thereof, and further oxidation of the other products of oxidation.

U.S. Pat. No. 3,231,608 (Kollar) discloses a process for the preparation of aliphatic dibasic acids from saturated cyclic hydrocarbons having from 4 to 8 cyclic carbon atoms per molecule in the presence of a solvent which comprises an aliphatic monobasic acid which contains only primary and secondary hydrogen atoms and a catalyst comprising a cobalt salt of an organic acid, and in which process the molar ratio of said solvent to said saturated cyclic hydrocarbon is between 1.5:1 and 7:1, and in which process the molar ratio of said catalyst to said saturated cyclic hydrocarbon is at least 5 millimoles per mole.

U.S. Pat. No. 3,161,603 (Leyshon et al.) discloses a process for recovering the copper-vanadium catalyst from the waste liquors obtained in the manufacture of adipic acid by the nitric acid oxidation of cyclohexanol and/or cyclohexanone.

U.S. Pat. No. 2,565,087 (Porter et al.) discloses the oxidation of cycloaliphatic hydrocarbons in the liquid phase with a gas containing molecular oxygen and in the presence of about 10% water to produce two phases and avoid formation of esters.

U.S. Pat. No. 2,557,282 (Hamblet et al.) discloses production of adipic acid and related aliphatic dibasic acids; more particularly to the production of adipic acid by the direct oxidation of cyclohexane.

U.S. Pat. No. 2,439,513 (Hamblet et al.) discloses the production of adipic acid and related aliphatic dibasic acids and more particularly to the production of adipic acid by the oxidation of cyclohexane.

U.S. Pat. No. 2,223,494 (Loder et al.) discloses the oxidation of cyclic saturated hydrocarbons and more particularly to the production of cyclic alcohols and cyclic ketones by oxidation of cyclic saturated hydrocarbons with an oxygen-containing gas.

U.S. Pat. No. 2,223,493 (Loder et al.) discloses the production of aliphatic dibasic acids and more particularly to the production of aliphatic dibasic acids by oxidation of cyclic saturated hydrocarbons with an oxygen-containing gas.

German Patent DE 44 26 132 A1 (Kysela et al.) discloses a method of dehydration of process acetic acid from liquid-phase oxidation of cyclohexane with air, in the presence of cobalt salts as a catalyst after separation of the adipic acid after filtration, while simultaneously avoiding cobalt salt precipitates in the dehydration column, characterized in that the acetic acid phase to be returned to the beginning of the process is subjected to azeotropic distillation by the use of added cyclohexane, under distillative removal of the water down to a residual content of less than [sic] 0.3–0.7%.

PCT International Publication WO 96/03365 (Constantini et al.) discloses a process for recycling a cobalt-containing catalyst in a direct reaction of oxidation of cyclohexane into adipic acid, characterized by including a step in which the reaction mixture obtained by oxidation into adipic acid is treated by extraction of at least a portion of the glutaric acid and the succinic acid formed during the reaction.

The patent literature is inconsistent and at least confusing regarding addition or removal of water in oxidations. For example:

U.S. Pat. No. 5,221,800 (Park et al.) discloses a process for the manufacture of adipic acid. In this process, cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to about 150° C. at an oxygen partial pressure of about 50 to 420 pounds per square inch absolute.

U.S. Pat. No. 4,263,453 (Schultz et al.) discloses a process claiming improved yields by the addition of water at the beginning of the reaction, generally of the order of 0.5 to 15% relative to monobasic aliphatic acid solvent, and preferably 1 to 10% relative to the solvent.

U.S. Pat. No. 3,390,174 (Schultz et al.) discloses a process claiming improved yields of aliphatic dibasic acids when oxidizing the respective cyclic hydrocarbons at temperatures between 130° and 160° C., while removing the water of reaction substantially as quickly as it is formed.

None of the above references, or any other references known to the inventors disclose, suggest or imply, singly or in combination, control of oxidation reactions by adjusting the water level subject to the intricate and critical controls and requirements of the instant invention as described and claimed.

Our U.S. Pat. Nos. 5,580,531, 5,558,842, 5,502,245, and our co-pending applications Ser. No. 08/477,195 (filed Jun. 7, 1995), Ser. No. 08/587,967 (filed Jan. 17, 1996), and Ser. No. 08/620,974 (filed Mar. 25, 1996), all of which are incorporated herein by reference, describe methods and apparatuses relative to controlling reactions in atomized liquids. Our co-pending application, Ser. No 08/812,847, filed on Mar. 6, 1997, and our co-pending application, Ser. No. 08/824,992, filed on Mar. 27, 1997 are both also incorporated herein by reference.

All of the following patent applications, which were filed simultaneously on May 21, 1997, are also incorporated herein by reference:

U.S. patent application Ser. No. 08/861,281 of Mark W. Dassel, Eustathios Vassiliou, David C. DeCoster, Ader M. Rostami, and Sharon M. Aldrich, titled "Methods and Devices for Controlling the Reaction Rate of a Hydrocarbon to an Intermediate Oxidation Product by Monitoring Flow of Incoming and Outcoming Gases";

U.S. patent application Ser. No. 08/861,180 of David C. DeCoster, Ader M. Rostami, Mark W. Dassel, and Eustathios Vassiliou, titled "Methods and Devices for Controlling the Oxidation Rate of a Hydrocarbon by Adjusting the Ratio of the Hydrocarbon to a Rate-Modulator";

U.S. patent application Ser. No. 08/861,176 of Mark W. Dassel, Eustathios Vassiliou, David C. DeCoster, and Ader M. Rostami, titled "Methods of Preparing an Intermediate Oxidation Product from a Hydrocarbon by Utilizing an Activated Initiator";

U.S. patent application Ser. No. 08/859,890 of Ader M. Rostami, Mark W. Dassel, Eustathios Vassiliou, David C. DeCoster, titled "Methods and Devices for Controlling the Oxidation of a Hydrocarbon to an Acid by Regulating Temperature/Conversion Relationship in Multi-Stage Arrangements"; and U.S. patent application Ser. No. 08/861,210 of Eustathios Vassiliou, Ader M. Rostami, David C. DeCoster, and Mark W. Dassel, titled "Pseudo-Plug-Flow Reactor."

SUMMARY OF THE INVENTION

As aforementioned, this invention relates to methods and devices for oxidizing hydrocarbons, such as cyclohexane for example, to respective acids, such as adipic acid for example, by a direct process. Particularly, it pertains a method of controlling in a reaction zone the oxidation of a hydrocarbon to form an acid, the oxidation occurring in the presence of a catalyst, a solvent, an optional initiator, water, and oxidation products. The hydrocarbon, the catalyst, the solvent, the water, and at least part of the oxidation products form a substantially single-phase liquid mixture, which liquid mixture may or may not contain a separate solid phase. The method comprises the steps of:

(a) contacting the substantially single-phase liquid mixture with a gaseous oxidant in the reaction zone at a first temperature, the first temperature being adequately high for the oxidation to proceed;

(b) driving the oxidation to a steady state at a water level; and (c) controlling the water level in a range between a maximum level of water, over which maximum level the substantially single liquid phase is transformed to two liquid phases, and a minimum level under which minimum level catalyst precipitates.

This invention is very important because in the regions discovered and claimed, outstanding performance is achieved, including, but not limited to highly improved reactivity, selectivity, and yield.

The range in step (c) may be divided into a higher portion and a lower portion, the higher portion of the range being between the maximum level and the average value of the maximum and minimum levels, while the lower portion of the range being between the minimum level and the average value of the maximum and minimum levels, and wherein the water level may be controlled within the higher portion. Also, the range in step (c) may be divided as above, and the water level may be controlled within the lower portion.

In the embodiments described herein, the amount of water present includes amounts of water introduced by other means, such as the crystalline water of cobalt(II) acetate tetrahydrate, for example, unless otherwise specified. In the case that the water, such as crystalline water for example, is not accounted for as being part of the water level, then it is accounted for as being part of the entity that it introduces it, such as catalyst for example. This invention encompasses both cases. Control may be achieved by either taking into account additional water, such as for example the crystalline water of the catalyst, or by not accounting for such additional water, depending on the particular situation.

By the term "steady state" it is meant that the reaction has reached an equilibrium, which equilibrium, however, may be adjusted periodically or continuously in order to achieve a desired result. If for example more water is needed in the reaction zone to avoid catalyst precipitation, the water feed rate to the reaction zone may be increased appropriately, and still the reaction may be considered to be at a "steady state." Similarly, if less water is needed to avoid formation of two phases, the water feed rate to the reaction zone may be decreased appropriately, and still the reaction may be considered to be at a "steady state."

The terms "substantially single-phase liquid" and "substantially single liquid phase" are for all practical purposes synonymous for the purposes of this invention. They both intend to indicate that there is no second liquid phase present, while a solid phase may or may not be present. The terms "second phase formation" or "formation of a second phase" refer to a second liquid phase, and not to a solid phase, unless otherwise specified.

The term "level" of an ingredient (reactant, reaction product, inert matter, or any other type of matter present) includes both "relative level" and "percentage level." According to the instant invention, both methods and devices may perform by using either one or the other type of "levels." In some occasions it may be easier to use one type rather than the other. "Relative level" of an ingredient denotes the amount of the ingredient present in weight units or in volume units, in a reaction zone or in a cell for example, as compared to 100 units, in weight units or in volume units, respectively, of the rest of the ingredients present, or the rest of the ingredients under consideration. The rest of the ingredients present or the rest of the ingredients under consideration, in this case, have a constant ratio with respect to each other. On the other hand, "percentage level" is the level expressed as a percentage based on total amount of all or of a desired number of specific ingredients. The percentages may be expressed also either by weight or by volume.

A controller, preferably a computerized controller, may handle with ease and accuracy either type of "level." Programming a computerized controller to perform such functions is a routine process, well known to the art. According to this invention, a controller, based on information received, from a reaction zone for example, controls feed rates, temperatures, pressures, and other parameters in order to achieve the desirable results. Since the raw results regarding the point of a second liquid phase formation (which results are received from a cell, such as the cells shown in FIGS. 2, 2A, and 2B, which will be discussed in detail at a later section) are obtained in relative levels, maintenance or adjustments in the reaction zone are more accurate when "relative levels" are used. The controller may also be programmed, by well known to the art techniques, to include flow sheet simulation, which may account for vapor/liquid equilibrium and energy balance effects.

Preferably, the first temperature is maintained within desired limits by controlling evaporation rate of condensible volatile matter contained in the reaction zone. The evaporation rate of the condensible volatile matter may be controlled by adjusting the content of the condensible volatile matter in the reaction zone. The evaporation rate of the condensible volatile matter may also be controlled by adjusting flow rate of non-condensible gases passed through the reaction zone. The evaporation rate of the condensible volatile matter may also be controlled by adjusting the pressure within the reaction zone.

It is preferable that at least part of the evaporated condensible volatile matter is recirculated to the reaction zone.

The energy balance in the reactor device may be achieved in the manner described above, with or without the use of internal and/or external cooling devices, such as cooling coils for example.

Controlling the water level under the upper limit may be achieved by removing water from the reaction zone by evaporation. Further, controlling the water level above the lower limit may be achieved by adding water to the reaction zone, including recirculating water which was evaporated from the reaction zone. Controlling the water level within the upper and lower limits may be based on determining the composition of the reaction zone, comparing said composition with phase diagrams, and adding water to the contents of the reaction zone if the lower limit is being approached or removing water from the contents of the reaction zone if the upper limit is being approached. Controlling the water level within the upper and lower limits may also be based on sampling the contents of the reaction zone, conducting indicative tests, as described herein, to determine a water level position within the composition of said contents with respect to the upper and the lower limits, and adding or removing water from said contents, accordingly, if so desired.

Controlling the water level in the reaction zone to be over the minimum level under which catalyst precipitates, may comprise a step of taking a sample from the reaction zone, raising the temperature of the sample by a predetermined degree above the first temperature, and if catalyst precipitation occurs increase the level of water in the reaction zone.

According to this invention, it is preferable that the hydrocarbon comprises cyclohexane, the catalyst comprises a cobalt compound, the solvent comprises acetic acid, the initiator comprises a compound selected from a group consisting of cyclohexanone, cyclohexylhydroperoxide, acetaldehyde, and a mixture thereof, and the gaseous oxidant comprises oxygen.

Further, the instant invention pertains to a method, wherein the acid comprises a compound selected from a group consisting of adipic acid, phthalic acid, isophthalic acid, and terephthalic acid, and the method further comprises a step of reacting the acid with a third reactant selected from a group consisting of a polyol, a polyamine, and a polyamide in a manner to form a polymer of a polyester, or a polyamide, or a (polyimide and/or polyamideimide), respectively.

The present invention also pertains a device for controlling the oxidation of a hydrocarbon to form an acid, which oxidation occurs in the presence of a catalyst, a solvent, an optional initiator, water, and oxidation products. The hydrocarbon, the catalyst, the solvent, the water, and at least part of the oxidation products form a substantially single-phase liquid mixture, which liquid mixture may or may not contain a separate solid phase. The device comprises:

a reaction chamber;

liquid feeding means for feeding at least partially the hydrocarbon, the solvent, the optional initiator, and optionally water into the reaction chamber;

water removing means for removing water from the reaction chamber;

gaseous feeding means for feeding oxidant into the reaction chamber; and water level control means for controlling the water level in a range between a maximum level of water, over which maximum level the substantially single-phase liquid mixture is transformed to two liquid phases, and a minimum level under which catalyst precipitates.

The water level control means may comprise water level detection means for detecting positioning of the water level with respect to the maximum level and the minimum level in the reaction zone. In turn, the device preferably comprises a controller connected to the water level detection means for receiving information regarding the positioning of the water level, and using said information for adjusting said water level in a manner to control said water level between the maximum level and the minimum level. The water level detection means may also comprise a temperature operated detector for detecting the positioning of the water level with respect to the maximum and minimum levels.

The water level control means may comprise analytical water level detection means for detecting and/or determining the water level in the reaction chamber. The device may further comprise a controller connected to the analytical water level detection means for receiving information regarding the water level in the reaction chamber, compare said information with phase diagram data stored in the controller, and using said comparison for adjusting said water level in a manner to control said water level between the maximum level and the minimum level in the reaction zone.

The device, preferably, also comprises solvent level control means, catalyst level control means, hydrocarbon level control means, along with respective detection means, all connected to the reaction chamber for detecting and controlling the feed rates of these ingredients, preferably through a controller, as shown later in the description of the preferred embodiments. These detectors may be individual or part of an analytical apparatus, which apparatus gives information to the controller for controlling the feed rates according to a predetermined program.

The reactor device of the present invention may comprise a condenser connected to the reaction chamber for removing heat from the liquid mixture. It may further comprise a decanter connected to the condenser for receiving condensed matter from the condenser and separating said condensed matter to a first liquid phase containing predominantly hydrocarbon and a second liquid phase containing predominantly water. In addition, the reactor device may further comprise a controller for controlling recirculation of the first phase and the second phase from the decanter to the reaction chamber, if so programmed.

The water level control means, preferably, comprise water level detection means for detecting positioning of the water level with respect to the maximum level and the minimum level. The controller is also, preferably, connected to the water level detection means for receiving information regarding the positioning of the water level, and using said information for adjusting said water level in a manner to control said water level between the maximum level and the minimum level in the reaction zone.

The instant invention is also related to a method of maintaining in a reaction zone, in which reaction zone oxidation of a hydrocarbon to an acid is conducted, a substantially single-phase liquid mixture comprising the hydrocarbon at a first hydrocarbon level, a catalyst at a first catalyst level, a solvent at a first solvent level, and water at a first water level, the method comprising the steps of:

(a) contacting the substantially single-phase liquid mixture with a gaseous oxidant in the reaction zone at a first temperature;

(b) taking a sample from the reaction zone;

(c) adding to the sample a component selected from a group consisting of water, hydrocarbon, catalyst, and a combination thereof, at a temperature equal to the first temperature until a second liquid phase is formed at a second water level, a second hydrocarbon level, a second catalyst level, or a combination level, respectively; and (d) controlling in the reaction zone, the water level, the hydrocarbon level, the catalyst level, and the combination level in the reaction zone at a lower level than the second water level, the second hydrocarbon level, the second catalyst level, and the combination level, respectively.

In the case of accidental or on purpose formation of a second liquid phase, for any reason, adequate bubbling of gaseous oxidant or any other cause of adequate turbulence in the reaction zone, will result in a representative sample, regardless of the position from which the sample is taken from the reaction zone, since the two liquid phases will be well distributed within each other, under such circumstances. Further, a high speed recirculation loop, and sampling from the loop, would be beneficial for sampling purposes.

In this case also, as in all previous and all following embodiments, it is preferable that the hydrocarbon comprises cyclohexane, the catalyst comprises a cobalt compound, preferably cobalt compound comprises cobalt acetate tetrahydrate, the solvent comprises acetic acid, the initiator comprises a compound selected from a group consisting of cyclohexanone, cyclohexylhydroperoxide, acetaldehyde, and a mixture thereof, and the gaseous oxidant comprises oxygen.

This invention also includes a method of maintaining in a reaction zone, in which reaction zone oxidation of a hydrocarbon to an acid is conducted, a substantially single-phase liquid mixture comprising the hydrocarbon at a first hydrocarbon level, a catalyst at a first catalyst level, a solvent at a first solvent level, and water at a first water level, the method comprising the steps of:

(a) contacting the substantially single-phase liquid mixture with a gaseous oxidant in the reaction zone at a first temperature;

(b) taking a sample from the reaction zone;

(c) adding to the sample a component selected from a group consisting of additional water, additional hydrocarbon, additional catalyst, and a combination thereof, at a temperature equal to the first temperature at least until a second liquid phase is formed at a second water level, or a second hydrocarbon level, or a second catalyst level, or a combination level, respectively;

(d) in sequence adding to the sample additional solvent, at a temperature equal to the first temperature, until a substantially single-phase liquid is formed again at a second solvent level, thus determining the second solvent level at which a substantially single liquid phase prevails at the second water level, or the second hydrocarbon level, or the second catalyst level, or at the combination level; and (e) controlling in the reaction zone the first solvent level in a manner to be maintained at the second solvent level or higher, if the second water level, or the second hydrocarbon level, or the second catalyst level, or the combination level are reached in the reaction zone, either on purpose, or unwillingly.

The instant invention also pertains to a method of determining the level of hydrocarbon, or of catalyst, or of water, or of a combination thereof, at which level, a second liquid phase is formed, the method comprising a step of adding to a sample (which contains the hydrocarbon at a first hydrocarbon level, the catalyst at a first catalyst level, the solvent at a first solvent level, and water at a first water level, at a first temperature and in a substantially single-phase liquid) a component selected from a group consisting of additional water, additional hydrocarbon, additional catalyst, and a combination thereof, at a temperature equal to the first temperature until a second liquid phase is formed at a second water level, or a second hydrocarbon level, or a second catalyst level, or a combination level, respectively.

This invention is further related to a method of determining in a sample (containing a hydrocarbon at a first hydrocarbon level, a catalyst at a first catalyst level, a solvent at a first solvent level, and water at a first water level, at a first temperature and in a substantially single liquid phase), a second level of solvent, which is the minimum level of solvent at which the single liquid phase is maintained, if at the first solvent level, the hydrocarbon attains a second hydrocarbon level, or the catalyst attains a second catalyst level, or the water attains a second water level or a combination of hydrocarbon, catalyst and water attains a second combination level, at which or under which second hydrocarbon level, or second catalyst level, or second water level or second combination level, a second liquid phase is formed, the method comprising steps of:

(a) adding to the sample a component selected from a group consisting of additional water, additional hydrocarbon, additional catalyst, and a combination thereof, at a temperature equal to the first temperature, at least until a second liquid phase is formed at the second water level, or the second hydrocarbon level, or the second catalyst level, or the second combination level, respectively; and (b) adding to the sample additional solvent, at a temperature equal to the first temperature, until a substantially single-phase liquid is formed again at the second solvent level, thus determining the second solvent level at which a substantially single liquid phase prevails at the second water level, or the second hydrocarbon level, or the second catalyst level, or at the second combination level.

Further, this invention pertains to a method of maintaining in a reaction zone, in which reaction zone oxidation of a hydrocarbon to an acid is conducted, a substantially single-phase liquid in a mixture comprising the hydrocarbon at a first hydrocarbon level, a catalyst at a first catalyst level, a solvent at a first solvent level, and water at a first water level, the method comprising the steps of:

(a) contacting the liquid mixture with a gaseous oxidant in the reaction zone at a first temperature, the first temperature being adequately high for the oxidation to proceed;

(b) taking a sample from the reaction zone; and (c) lowering the temperature of the sample to a predetermined second temperature, and if a second liquid phase is formed at a critical temperature in the range between the first and second temperatures, either decrease in the reaction zone the first level of one component selected from a group consisting of hydrocarbon, water, catalyst, and a mixture thereof to a degree that in a new sample a second liquid phase does not form in the range between the first and second temperatures, or increase in the reaction zone the first solvent level to a degree that in a new sample a second liquid phase does not form in the range between the first and second temperatures, or increase in the reaction zone the first temperature to a third temperature by at least the difference between the critical temperature and the second temperature, or a combination thereof.

This invention also relates to a method of determining (in a sample containing a hydrocarbon, dissolved catalyst, a solvent, and optionally water, at a first temperature) whether catalyst precipitates at a precipitation temperature, and determining said precipitation temperature if it occurs, the method comprising a step of confining the sample within a closed cell under adequate pressure to retain the sample in a substantially liquid form, raising the temperature from the first temperature to a higher temperature, at which higher temperature catalyst may precipitate, or to a temperature of 150° C. if catalyst does not precipitate up to 150° C., and detecting precipitation, if precipitation occurs at a precipitation temperature lower or equal to 150° C. It is preferable that detecting precipitation of catalyst is based on increased turbidity, or increased light absorption of the sample at the precipitation temperature.

A different embodiment of this invention relates to a device for controlling the oxidation of a hydrocarbon to form an acid, in the presence of a solvent, a catalyst, an optional initiator, and water in a substantially single-phase liquid mixture, the hydrocarbon in the mixture being at a first hydrocarbon level, the solvent being at a first solvent level, the catalyst being at a first catalyst level, and the water being at a first water level, the device comprising:

a reaction chamber enclosing a reaction zone;

liquid feeding means connected to the reaction chamber for feeding at least partially the hydrocarbon, the solvent, the catalyst, the optional initiator, and optionally water into the reaction zone;

gaseous feeding means connected to the reaction chamber for feeding oxidant in the reaction zone;

level control means for detecting one or more of a hydrocarbon second level, a catalyst second level, a water second level, and a combination second level, at which second level, a second liquid phase is formed; and a controller connected to the level control means for controlling in the reaction zone the level of the hydrocarbon, the level of catalyst, the level of water, and the level of the combination, at a level lower than the second level of the hydrocarbon, the second level of the catalyst, the second level of the water and the second level of the combination, respectively.

A still another embodiment relates to a device for controlling the oxidation of a hydrocarbon to form an acid, in the presence of a solvent, a catalyst, an optional initiator, and water in a substantially single-phase liquid mixture, the hydrocarbon in the mixture being at a first hydrocarbon level, the solvent being at a first solvent level, the catalyst being at a first catalyst level, and the water being at a first water level, the device comprising:

a reaction chamber enclosing a reaction zone;

liquid feeding means connected to the reaction chamber for feeding at least partially the hydrocarbon, the solvent, the catalyst, the optional initiator, and optionally water into the reaction zone;

gaseous feeding means connected to the reaction chamber for feeding oxidant in the reaction zone;

level control means connected to the reaction chamber for sampling the reaction zone and detecting a hydrocarbon second level, a catalyst second level, a water second level, and a combination second level, at which second level, a second liquid phase is formed; and solvent level control means connected to the reaction chamber or being part of the level control means for detecting a second solvent level, at and over which, the second liquid phase is eliminated at the hydrocarbon second level, or the catalyst second level, or the water second level, or the combination second level; and a controller connected to the solvent level control means for controlling in the reaction zone the solvent at a level higher than the second solvent level for maintaining a substantially single liquid phase in the reaction zone, if the water second level, or the hydrocarbon second level, or the catalyst second level, or the combination second level are reached in the reaction zone, either on purpose, or unwillingly.

A different embodiment pertains to a device for controlling the oxidation of a hydrocarbon to form an acid, in the presence of a solvent, a catalyst, an optional initiator, and water in a substantially single-phase liquid mixture, the hydrocarbon in the mixture being at a first hydrocarbon level, the solvent being at a first solvent level, the catalyst being at a first catalyst level, and the water being at a first water level, the device comprising:

a reaction chamber enclosing a reaction zone;

liquid feeding means connected to the reaction chamber for feeding at least partially the hydrocarbon, the solvent, the catalyst, the optional initiator, and optionally water into the reaction zone;

gaseous feeding means connected to the reaction chamber for feeding oxidant into the reaction zone;

reaction temperature controlling means for controlling a first temperature in the reaction zone;

a cell connected to the reaction chamber for sampling the substantially single-phase liquid mixture;

means for varying the temperature of the substantially single-phase liquid mixture in the cell so as to determine whether a critical temperature exists, at which critical temperature a second liquid phase is formed, the critical temperature being lower than the first temperature and higher than a predetermined second temperature;

a detector for detecting formation of a second liquid phase in the cell; and a controller connected to the detector for receiving information from said detector, the controller also being connected to the reaction temperature control means, the controller being programmed in a manner that if a critical temperature is detected, the first temperature in the reaction zone is increased by at least the difference between the critical temperature and the second temperature.

Still a different embodiment pertins to a device for controlling the oxidation of a hydrocarbon to form an acid, in the presence of a solvent, a catalyst, an optional initiator, and water in a substantially single-phase liquid mixture, the hydrocarbon in the mixture being at a first hydrocarbon level, the solvent being at a first solvent level, the catalyst being at a first catalyst level, and the water being at a first water level, the device comprising:

a reaction chamber enclosing a reaction zone;

liquid feeding means connected to the reaction chamber for feeding at least partially the hydrocarbon, the solvent, the catalyst, the optional initiator, and optionally water into the reaction zone;

gaseous feeding means connected to the reaction chamber for feeding oxidant in the reaction zone;

a cell connected to the reaction chamber for sampling the substantially single-phase liquid mixture;

means for varying the temperature of the substantially single-phase liquid mixture in the cell so as to determine whether a critical temperature exists, at which critical temperature a second liquid phase is formed, the critical temperature being lower than the first temperature and higher than a predetermined second temperature;

a detector for detecting formation of a second liquid phase in the cell; and a controller connected to the detector for receiving information from said detector, the controller also being connected to the liquid feeding means, the controller being programmed in a manner that if a critical temperature is detected, one or more of the first levels of the hydrocarbon, the water, and the catalyst is (are) decreased or the first level of the solvent is increased to second level(s), respectively, at which second level(s) the critical temperature disappears by falling under the second temperature.

This invention also pertains to a monitor for detecting formation of a second liquid phase in a mixture containing hydrocarbon, and one or more of solvent, catalyst, and water, the monitor comprising:

a cell for containing the mixture;

means for introducing hydrocarbon, and/or solvent, and/or catalyst, and/or water into the cell; and a detector for detecting presence or formation of a second liquid phase in the mixture within the cell upon addition of hydrocarbon and/or solvent, and/or catalyst, and/or water into the cell.

Preferably, the detector is an optical device or a conductivity device. The detector, regardless of whether it is an optical device, a conductivity device, or any other type of device, may be a single detector, or a multiplicity of detectors. Also, a single monitor may be used or a plurality of monitors.

Another embodiment relates to a monitor for detecting formation of a second liquid phase in a mixture containing hydrocarbon, and one or more of solvent, catalyst, and water, the monitor comprising:

a cell for containing the mixture at a temperature;

temperature control means for varying the temperature of the mixture in the cell; and a detector for detecting presence or formation of a second liquid phase in the mixture within the cell, upon varying the temperature of the mixture.

As in the previous case, preferably, the detector is an optical device or a conductivity device. The detector, regardless of whether it is an optical device, a conductivity device, or any other type of device, may be a single detector, or a multiplicity of detectors. Also, a single monitor may be used or a plurality of monitors.

This invention also pertains to a monitor for detecting precipitation of catalyst in a mixture containing hydrocarbon, catalyst, solvent, and optionally water, the monitor comprising:

a cell for containing the mixture at a temperature;

temperature control means for varying the temperature of the mixture in the cell; and a detector for detecting precipitation of catalyst, upon varying the temperature of the mixture.

Preferably, the detector in this case is an optical device.

According to this invention, the water level may further be restricted, for any reason, to either the higher portion or to the lower portion of the range between the maximum level of water, over which the single liquid phase is transformed to two liquid phases, or the minimum level, under which catalyst precipitates. For example, largest possible amounts of water (without formation of a second liquid phase) may be desired for easier hydrolysis or minimization of esters produced as by-products during the oxidation, while lowest possible amounts of water (without catalyst precipitation) may be desired for higher reaction rates. The higher portion of the range is between the maximum level and the average value of the maximum and minimum levels, while the lower portion of the range is between the minimum level and the average value of the maximum and minimum levels.

This invention also includes a method of controlling in a reaction zone the oxidation of a hydrocarbon to form an acid, the oxidation occurring in the presence of a catalyst, a solvent, an optional initiator, water, and oxidation products; the hydrocarbon, the catalyst, the solvent, the water, and at least part of the oxidation products forming a substantially single-phase liquid mixture in the presence or absence of a separate solid phase, the method comprising the steps of:

(a) contacting the liquid mixture with a gaseous oxidant in the reaction zone at a first temperature, the first temperature being adequately high for the oxidation to proceed;

(b) driving the oxidation to a steady state at a hydrocarbon first level; and (c) controlling the hydrocarbon first level to remain lower than a second hydrocarbon level, at or over which the substantially liquid phase is transformed to two liquid phases and/or catalyst precipitation occurs within said substantially single liquid phase.

The above method may also include the steps of:

(d) taking a sample from the reaction zone;

(e) maintaining the sample at substantially the first temperature;

(f) adding hydrocarbon to the sample;

(g) determining a second level of hydrocarbon in the sample, at which second level either the substantially single phase is transformed to two liquid phases, or catalyst is precipitated within the substantially single phase, or both; and (h) adjusting the first level in the reaction zone to remain under the second level, if th e first level approaches the second level.

As aforementioned, these methods are particularly suited in case that the hydrocarbon comprises cyclohexane, the solvent comprises acetic acid, and the catalyst comprises a cobalt salt.

BRIEF DESCRIPTION OF THE DRAWINGS

The reader's understanding of this invention will be enhanced by reference to the following detailed description taken in combination with the drawing figure, wherein.

1, and which may also be utilized for determining conditions for maintaining a substantially single liquid phase during oxidation of a hydrocarbon.

Figure 1:
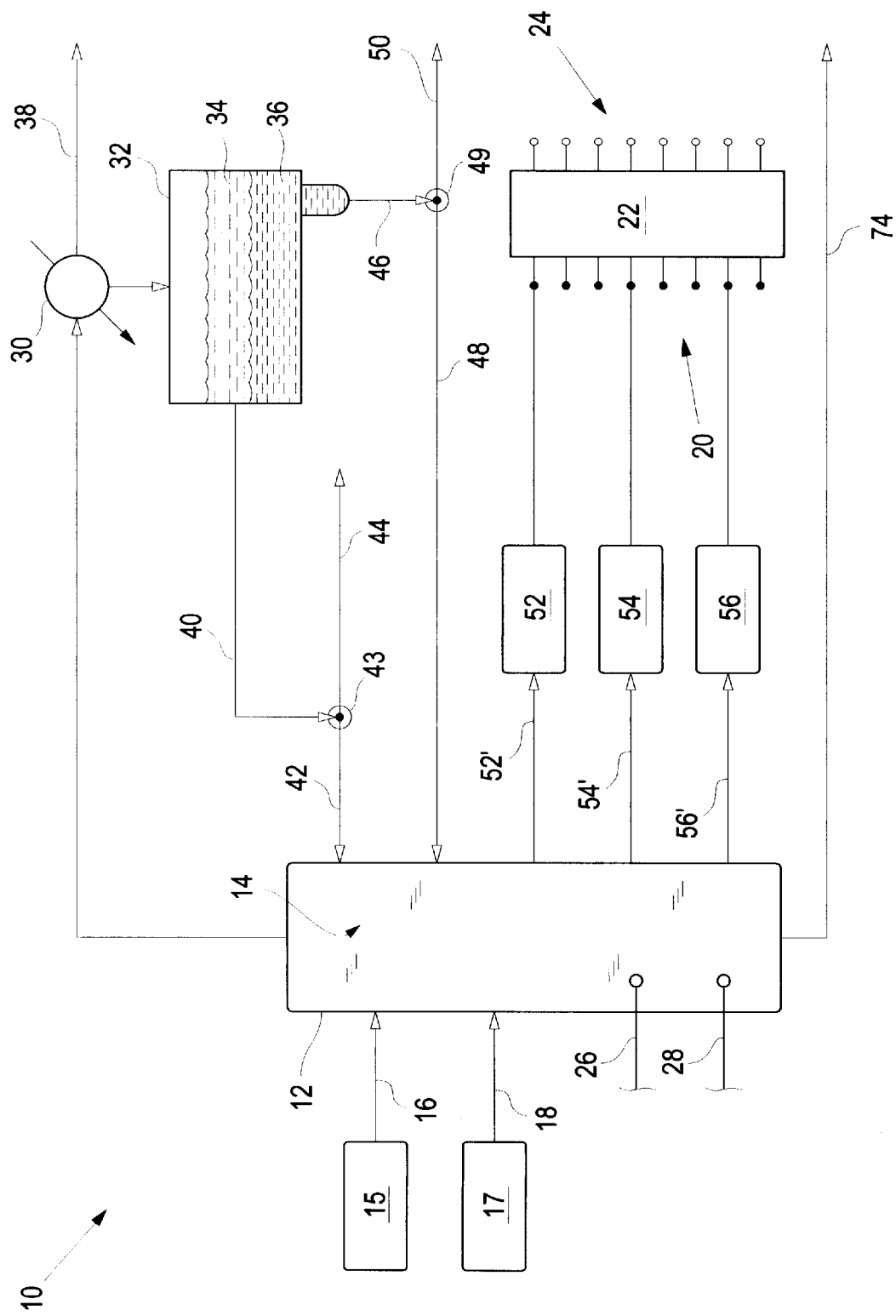
FIG. 1 illustrates a block diagram of a preferred embodiment of the present invention.
Figure 2B:
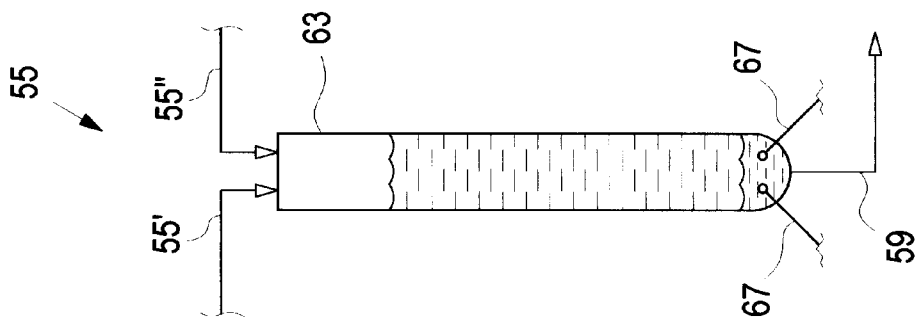
FIG. 2 illustrates schematically an upper water level monitor, which may be utilized in the embodiment of FIG.
Figure 2A:
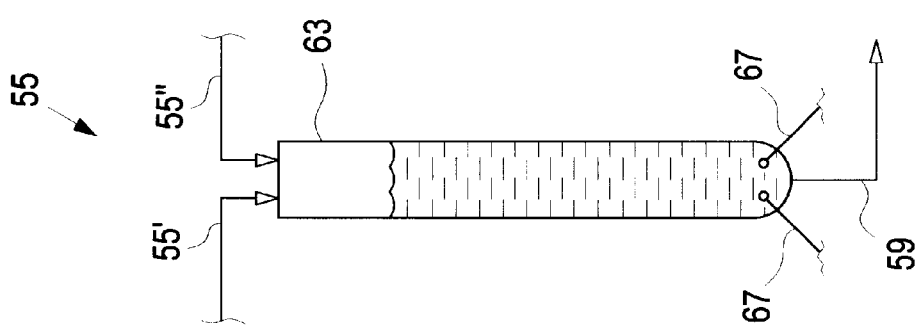

FIG. 2A illustrates schematically an upper water level monitor, based on conductivity measurements, which may be utilized in the embodiment of FIG. 1, and which may also be utilized for determining conditions for maintaining a substantially single liquid phase during oxidation of a hydrocarbon. The monitor is shown under conditions of a substantially single liquid phase.

FIG. 2B illustrates schematically the same upper water level monitor, based on conductivity measurements, as shown in FIG. 2A under conditions of a second liquid phase formation.

Figure 2:
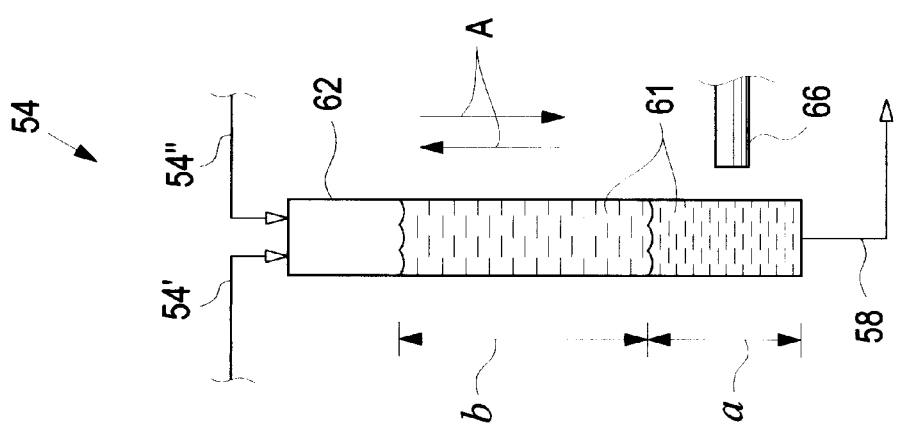
Figure 3:
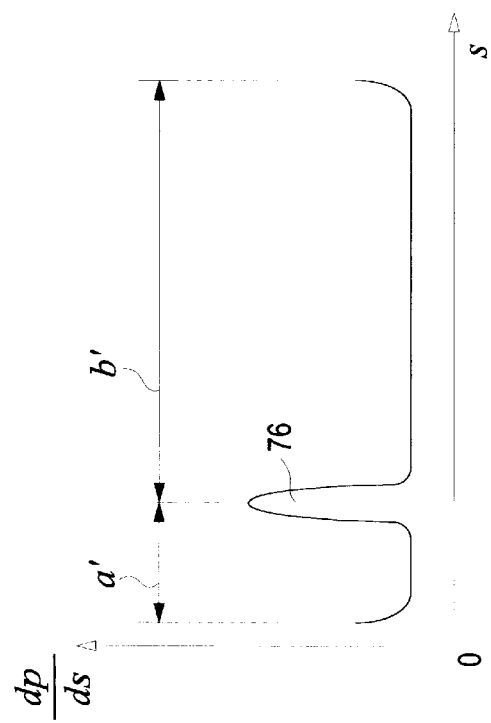

FIG. 3 illustrates a graph received by a detector used to scan a cell included in the upper water level monitor of FIG. 2.

Figure 4B:
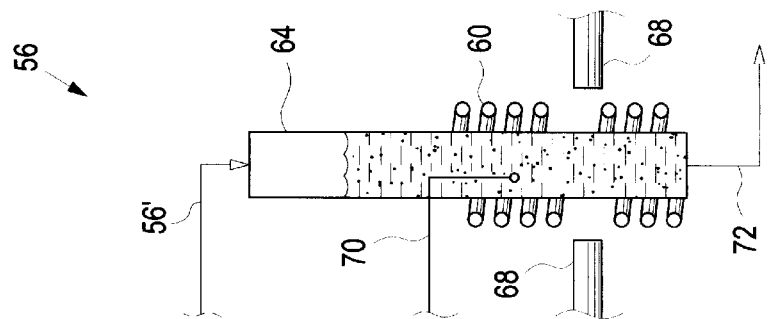
Figure 4A:
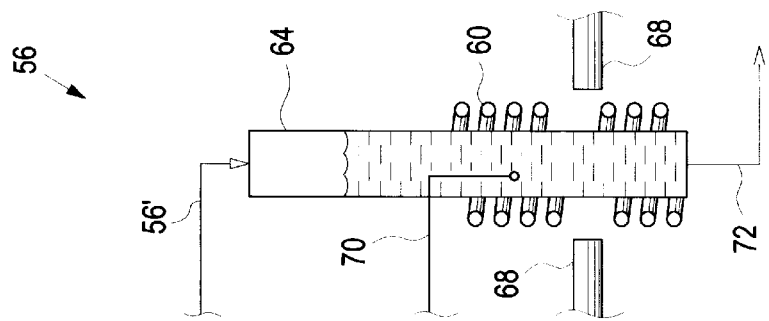

FIG. 4A illustrates schematically a lower water level monitor, which includes a second cell, before catalyst precipitation after a predetermined rise in temperature.

FIG. 4B illustrates schematically the same lower water level monitor of FIG. 4A, after catalyst precipitation.

Figure 5:
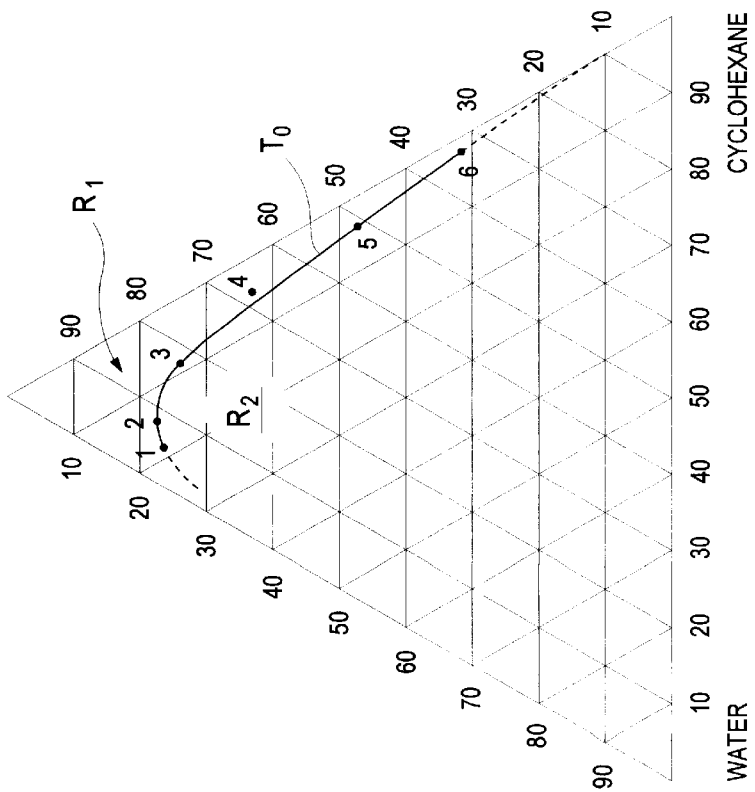

FIG. 5 shows a ternary phase diagram of (Acetic Acid)/(Cyclohexane)/(Water) at 100° C. at 0% level of cobalt acetate tetrahydrate.

Figure 6:
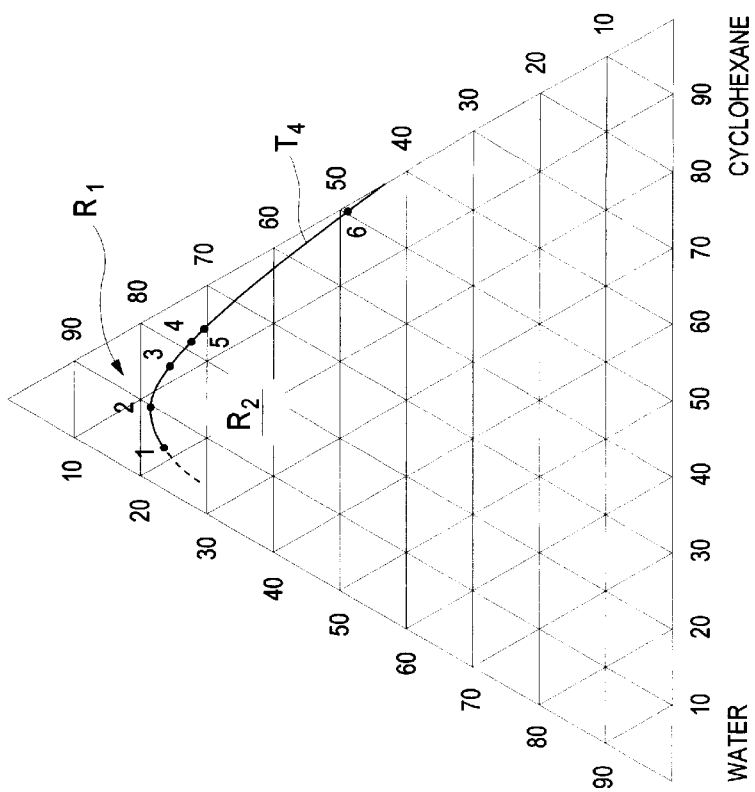

FIG. 6 shows a ternary phase diagram of (Acetic Acid)/(Cyclohexane)/(Water) at 100° C. at 4% level of cobalt acetate tetrahydrate.

Figure 7:
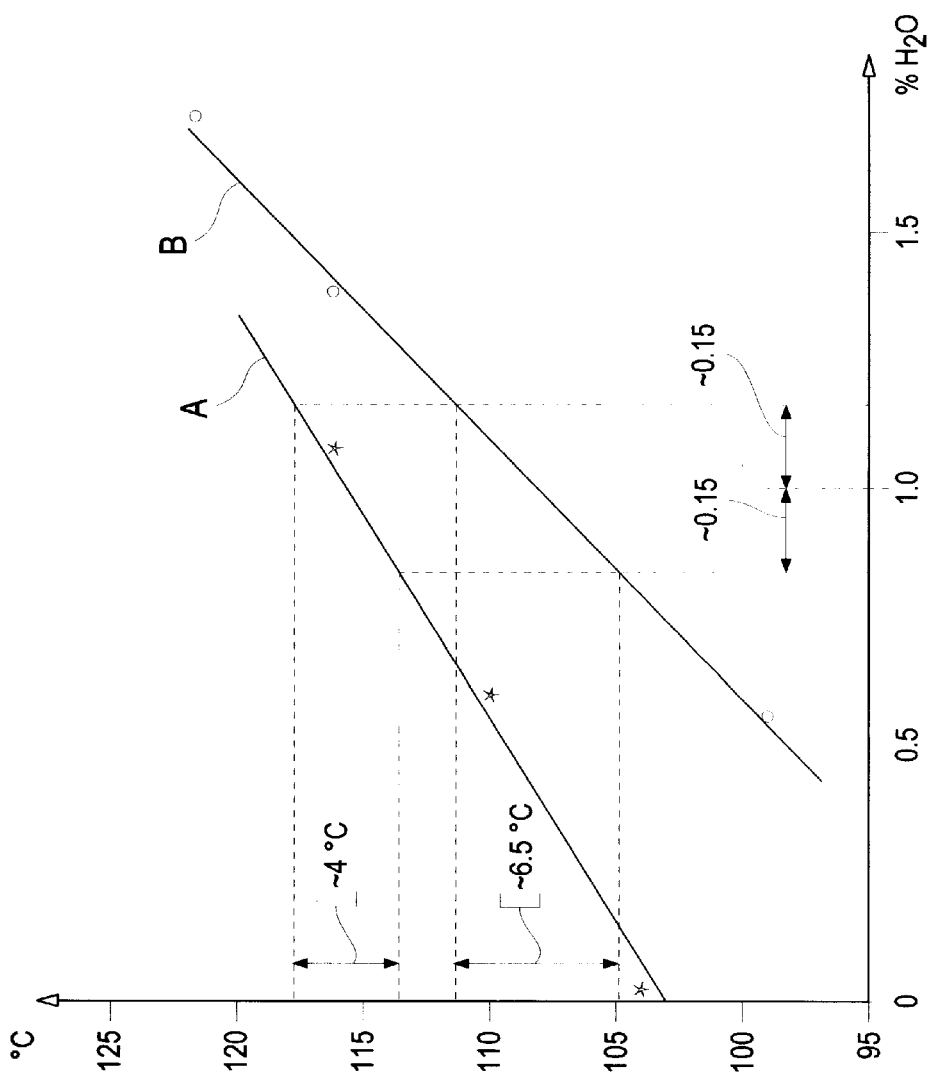

FIG. 7 shows a chart, which illustrates an example on how the predetermined rise in temperature in the second cell of the monitor of FIG. 4A may be determined.

DETAILED DESCRIPTION OF THE INVENTION

As aforementioned, this invention relates to methods and devices for oxidizing hydrocarbons, such as cyclohexane for example, to respective acids, such as adipic acid for example, by a direct process.

We have discovered that the unexpected combination of two critical phenomena is of utmost importance in the successful oxidation of a hydrocarbon, such as cyclohexane for example, to an acid, such as adipic acid for example.

The first of the two critical phenomena is the formation of a second liquid phase during the time that the reaction is taking place. Ways to maintain a substantially single-phase liquid during the oxidation are discussed in our co-pending application Ser. No 08/812,847, filed on Mar. 6, 1997, and our co-pending application, Ser. No. 08/824,992, filed on Mar. 27, 1997. If a second liquid phase is formed during the time that the reaction is taking place, the reaction rate drops to unacceptable levels, followed by unacceptably slow conversion rates, poor yields, and resulting in a totally uneconomical operation for all practical purposes.

The second of the two critical phenomena is catalyst precipitation during the time that the reaction is taking place. Catalyst precipitation during the time that the reaction is taking place has similar results as the formation of a second liquid phase.

Even in a case that only partial precipitation of catalyst takes place, this precipitation results in catalyst deposition on different parts of the reactor system, plugging of pipes and valves, etc. Reaction rate and reactivity also suffer upon catalyst precipitation.

Thus, there is a severe problem in the state of the present art, when the reaction conditions permit either catalyst precipitation or formation of a double liquid phase.

We have found that under a given set of conditions, the amount of water in a liquid reaction mixture during a steady state oxidation of a hydrocarbon to a respective acid, has to be controlled within critical limits defined by the point of a second liquid phase formation and the point of catalyst precipitation. We have also found that under a given set of conditions, there is a minimum level of water under which the catalyst, cobalt acetate for example, precipitates, and over which the catalyst remains in solution. By the same token, we have found that there is a maximum level of water over which a second liquid phase is formed, and under which the substantially single-phase liquid is maintained. Therefore, for a given set of conditions, it is imperative that the water level, in a liquid mixture undergoing oxidation, is controlled between a maximum level of water over which maximum level the substantially single-phase liquid is transformed to two liquid phases, and a minimum level, under which minimum level, catalyst is precipitated. The problem becomes more severe as the catalyst, cobalt acetate tetrahydrate for example, content increases, and also as the hydrocarbon, cyclohexane for example, content increases.

We also unexpectedly found that the catalyst, such as cobalt acetate tetrahydrate or cobalt 2-ethyl hexanoate for example, has a tendency to precipitate at higher temperatures rather than lower temperatures, despite the general trend of materials to be more soluble at higher temperatures rather than lower temperatures.

This unexpected finding is extremely important because it may be used to detect a level of water at which the point of catalyst precipitation is being approached, and additional water be added to avoid catalyst precipitation, as will be described in detail hereinbelow.

Referring now to FIG. 1, there is depicted a reactor system or device 10, comprising a reaction chamber 12 containing a reaction zone 14. The reactor system 10 is only partially shown for demonstrating the components necessary to exemplify the present invention. Miscellaneous treatment, product or by-product separation, recycling, etc. devices, well known to the art, are not shown for purposes of clarity and brevity.

The reaction chamber 12 encloses a reaction zone 14. Liquid feeding means 15 ending to a liquids feeding line 16 and gaseous feeding means 17 ending to an oxidant feeding line 18, are connected to the reaction chamber 12 for providing liquid feed and gaseous oxidant, respectively, to the reaction zone 14.

The reaction chamber 12 may be a stirred-tank reactor, atomization reactor, re-circulation reactor, or any other type of reactor, known to the art.

The liquids feeding line 16 may be a single line or a multiple line. The liquid feeding means 15 may include heat exchangers, pre-mixing vessels, flowmeters, thermocouples, etc., and they are connected (not shown for purposes of clarity and brevity) to one or more of inputs 20 of a controller 22. In turn the controller 22 is connected to the liquid feeding means 15, through one of its outputs 24, and controls its operation by methods well known to the art.

In a similar manner, the gaseous feeding means 17 are connected (not shown for purposes of clarity and brevity) to one or more of inputs 20 of a controller 22. In turn the controller 22 is connected to the liquid gaseous oxidant means 17, through one of its outputs 24, and controls its operation by methods well known to the art. Further, temperature monitor 26 and pressure monitor 28 are connected to the reaction chamber 12 for monitoring the temperature and the pressure in the reaction zone 14. They give relevant information to the controller 22 through input lines (not shown) connected to respective inputs 20 of the controller 22, so that the controller 22 adjusts the temperature and pressure of the reaction zone 14 in the reaction chamber 12, according to a predetermined way programmed in the controller 22, by well known to the art techniques.

A condenser 30 is also connected to the reaction chamber 12. One of the main purposes of the condenser 30 is to remove heat from the reaction zone 14. Vapors of condensibles, such as for example hydrocarbon, solvent, water, and the like may be refluxed directly to the reaction zone 14 of the reaction chamber 12, or they may be directed to a decanter 32, where they may be separated to an upper phase 34 and a lower phase 36. Off gases follow line 38 for preferably being scrubbed in order to remove escaping condensibles, and in turn they are usually freed to the atmosphere. Of course, in certain occasions, preferably before scrubbing, they are at least partially recycled to the reaction zone 14 of the reaction chamber 12. When recycled to the reaction zone, they may be introduced, partially or totally, under the liquid surface for supplemental sparging and/or reaction.

The decanter 32 is connected to line 40, which in turn communicates totally or partially with lines 42 and 44 through first valve 43. Thus, upper phase 34 liquids are partially or totally recycled to the reaction chamber 12, and/or partially or totally removed through line 44, usually for further treatment. The decanter 32 is also connected to line 46, which in turn communicates totally or partially with lines 48 and 50 through second valve 49. Thus, lower phase 36 liquids are partially or totally recycled to the reaction chamber 12, and/or partially or totally removed through line 50, usually for further treatment. The first valve 43 and the second valve 49 are preferably controlled by controller 22, so that desired feeding rates of each phase are either recycled to the reaction chamber 12 or they are directed for treatment and/or disposal.

Instead of the condenser 30 and the decanter 32, a distillation column (not shown) may be used for considerably better separation of the different condensible components, such as for example hydrocarbon, solvent, water, by-products, etc. Thus, the distillation column may be used in the same manner as the combination of the condenser and the decanter for both removing heat and for separation of the individual condensible components.

An analytical apparatus 52 is also connected to the reaction chamber 12 through line 52'. The analytical apparatus 52 is programmed by the controller 22 to take samples from the reaction chamber 12 and analyze them. This analytical apparatus preferably comprises HPLC and GC equipment, well known to the art, and it may be used to determine water, solvent, hydrocarbon, catalyst, oxidation products, oxidation by-products, etc. Of course, sampling of the contents of the reaction chamber 12 may be manual, with subsequent feeding to the analytical apparatus and then feeding the analysis results to the controller 22 for further processing.

In addition to or in place of the analytical apparatus 52 there is an upper water level monitor 54 and a lower water level monitor 56 connected to the reaction chamber 12. Samples from the contents of the reaction chamber 12 are provided to the monitors 54 and 56 through lines 54' and 56', respectively. As above, this operation may also be manual and/or be based on visual observations, as it will be explained in more detail later. Further, the results from the two monitors 52 and 54 may be fed automatically or manually to the controller 22. It is worth noting that the upper water level monitor 54 may also serve as a more versatile monitor for detecting the level of hydrocarbon, and/or the level of catalyst, in addition to or instead of the level of water, at which level, a second liquid phase is formed. It may also serve to determine a higher second solvent level at or over which the substantially single-phase liquid is maintained or re-established in the reaction zone, despite rise in hydrocarbon level and/or catalyst level and/or water level, which rise would have resulted in formation of a second liquid phase if the solvent had remained at its initial level.

An example of an upper water level monitor 54 is better shown in FIG. 2. The upper limit water level monitor may comprise an at least partially transparent first cell 62 for accepting liquid from the reaction chamber 12 through line 54', and a first detector 66 adapted to move up and down the height of the first cell 62, in order to detect the presence of more than one liquid phases 61. The monitor 54 is also supplied with line 54", through which plain water or water from line 48 containing solvent, may be introduced to the monitor 54 in predetermined amounts (the amount of solvent is usually higher than the amount of water in the lower phase, and weight ratios of solvent to water of about 75 to 25 are within reality). An exit line 58 is used to remove the liquids from the first cell 62 after a determination has been made, and a new determination is due. The monitor 54 may also be provided with a mixing mechanism (not shown for purposes of clarity), which may be based on stirring, shaking, mixing, and any other techniques well known to the art. Vigorous mixing is preferred.

The nature of the first cell 62 of monitor 54 is preferably such as to accept high pressures, preferably similar to the reaction pressures. However, low pressures are also acceptable, as long as the contents (except for gases) of the cell do not substantially volatilize. For this purpose, it is highly preferable that the cell is as full as possible with sample during its operation, which will be discussed in detail later. The first detector 66 can be a color detector, a refractive index detector, an ultrasonic detector, or in general, any type of detector that can distinguish and differentiate between liquids by using a property of the two liquids, which property may differentiate one from the other.

If the phases 61 separate to a lower phase having a height "a", and to an upper phase having a height "b", the differential of the detected property per scanned distance dp/ds ("p" being the property, such as color for example, and "s" being the scanning distance as shown by the arrows A) will give a graph as shown in FIG. 3, wherein a'/b'=a/b, from which the creation or presence and the degree of second liquid phase formation may be determined.

If the phases are difficult to separate into distinct portions, additional techniques to aid such separation may be utilized. Centrifuging, ultra-centrifuging, addition of flocculation agents, and the like, are examples of such techniques.

Although in FIG. 2 the first detector 66 is shown to reside outside the first cell, it may very well reside inside the first cell 62. A conductivity detector is an example of a detector that should come in contact with the liquid and preferably be inside, and more preferably at the bottom of the first cell 62.

The first detector may be a single detector traveling up and down the height of the first cell, or otherwise scanning the first cell, or it may be two or more detectors located steady at different positions of the first cell. In the case of using two detectors, it is preferable to arrange one detector in the vicinity of the bottom of the first cell and one detector in the vicinity of the top of the first cell. It is obvious that in the case of relative movement of the detector with respect to the first cell, the first cell may be the moving element and the detector the steady element. Instead of utilizing a detector, an observer may visually detect the creation or presence and the levels of the two liquid phases and provide this information to the controller 22.

When two liquid phases are formed and are difficult to separate, the first detector 66 may also be based on measuring or detecting the turbidity (cloudiness) of the mixture, if one liquid phase is dispersed or emulsified in the other liquid phase, since the two phases, for all practical purposes and substantially always, will have different indices of refraction. A substantially single-phase liquid will be clear, but a second liquid phase dispersed or emulsified in the first liquid phase will produce a turbid mixture. Care will have to be taken in this case to filter out any solid matter before determination of the turbidity. Light scattering may also be used for detection of a finely emulsified second liquid phase in a first phase.

Another example of an upper water level monitor 55, based on conductivity detection, is shown in FIGS. 2A and 2B, and comprises a cell 63 similar to cell 62 of monitor 54 (FIG. 2). In the vicinity of the bottom of cell 63, there are located conductivity leads, which measure conductivity, by well known to the art techniques. The cell 63 is also connected to a line 55' from which it may accept a sample from the reaction zone 14. It is further connected to line 55'' through which water may be introduced. Of course, if appropriate, line 55'' may be used for introduction of other liquids, such as for example hydrocarbon, catalyst, solvent, a mixture thereof, and the like. Line 59, connected to cell 63, is used as an exit line for the contents of cell 63, when they are not needed any further.

FIG. 2A shows one phase in the cell 63, while FIG. 2B shows a second liquid phase formation, which may be detected very easily by the conductivity probe 67, since the newly formed phase will have a highly different conductivity as compared to the one liquid phase system. Since the hydrocarbon, such as cyclohexane amount of dissolved solvent, such as acetic acid for example, the second liquid phase, which will be the polar phase, will place itself at the bottom of the cell 63, and it will give a highly increased conductivity. Thus, it will be detected very easily. More conductivity probes may be placed at different positions of the cell to detect the ratio of the two phases if so desired. In a case where the second liquid phase is expected to take place in the vicinity of the top of the cell 63, the conductivity probe may be placed in an accordingly appropriate position.

A low water level monitor 56 is better illustrated in FIGS. 4A and 4B. Monitor 56 comprises an at least semitransparent, and preferably transparent, second cell 64, which is provided with heating means, such as a heating coil 60 for example, and a second detector 68, which is capable of measuring light (preferably visible in this particular case) absorption, or turbidity, and the like, through a medium. The second cell 64 is also provided with a thermocouple 70 for monitoring the temperature of the contents of the second cell 64.

The second cell 64 is connected to line 56' from which it is provided with liquid mixture from the reaction zone 14 of the reaction chamber 12. An exit line 72 is used to remove the liquids from the second cell 64 after a determination has been made, and a new determination is due. The monitor 56 is preferably provided with a mixing mechanism (not shown for purposes of clarity), which may be based on stirring, shaking, mixing, and any other techniques well known to the art.

The second cell 64 is preferably such as to accept elevated pressures and temperatures as the case is for the first cell 62.

The analytical apparatus 52, shown in FIG. 1, may comprise one or more devices or one or more sets of devices for analyzing not only the composition of the reaction zone 14, but also the composition of miscellaneous streams.

A liquid transfer line 74 is connected to the reaction chamber 12 for removing flowable matter from the reaction zone 14 for removal of oxidation product, such as adipic acid for example, further treatment for removal of undesirable by-products, recycling of other matter, etc.

In operation of this embodiment, hydrocarbon, such as cyclohexane for example, solvent, such as acetic acid for example, catalyst, such as cobalt acetate tetrahydrate for example, and initiator such as cyclohexanone or acetaldehyde for example, are initially charged in the reaction zone 14 of the reaction chamber 12 through line 16. As mentioned earlier, line 16 may be a single line or a multiple line for introducing raw materials as a totality or as individual streams, or as combination of streams. A small amount of water (for example 0.2 to 2% by weight based on total charge, depending on individual circumstances) may also be added to the reaction zone 14. The raw materials may be introduced at reaction temperature, which reaction temperature in the case of preparation of adipic acid from cyclohexane is preferably in the range of 50 to 150° C., more preferably in the range of 80 to 130° C., and even more preferably in the range of 90 to 110° C. Alternatively, the raw materials may be introduced at a different temperature than the reaction temperature, preferably lower temperature, and then be brought to the reaction temperature by means of heating or cooling elements, accordingly, inside or outside the reaction chamber 12. In the case of a stirred-tank reactor, the reaction chamber is filled to a predetermined degree, preferably larger than half the capacity of the reaction chamber 12. In the case of an atomization reactor, preferably, a small charge at the bottom of the reaction chamber 12 is introduced, which is recirculated from upper levels of the reaction chamber 12 toward the bottom of the reaction chamber 12, in the form of a spray, as discussed in our aforementioned patents and applications dealing with atomization reactors. For purposes of simplicity, the following discussion will be predominantly directed to stirred-tank reactors.

The temperature is monitored by the temperature monitor 26, and the pressure by the pressure monitor 28. Temperature monitors, such as thermocouples for example, and pressure monitors, such as strain gauges, or coil gauges for example, are devices well known to the art. Information received from the temperature monitor 26 and the pressure monitor 28 is fed to the controller 22 through inputs 20. The monitor 22 adjusts in turn the temperature and the pressure in the reaction zone 14 in the reaction chamber 12 to stay within desired limits, by well known to the art techniques.

The pressure in the reaction zone 14 is preferably adjusted to be such that a large part of the hydrocarbon and of the solvent remain as liquids at the operation temperature. In the case of the direct oxidation of cyclohexane to adipic acid, pressures between 100 and 500 p.s.i.g. are usual, although they may range from a few p.s.i.g. to thousands of p.s.i.g. under certain circumstances.

During charging the raw materials, or after the desired charge has been completed, a gaseous oxidant starts being introduced through the oxidant feeding line 18. The gaseous oxidant is preferably either oxygen, or a mixture of oxygen with a substantially inert gas, such as nitrogen, carbon dioxide, noble gas, and the like. The partial pressure of oxygen is usually 10 to 300 p.s.i.g., although it may vary broadly outside this range, depending on the individual circumstances. The flow rate of the gaseous oxidant through line 18 is preferably adequately high in a manner to avoid oxidant starvation in the reaction zone 14.

As the gaseous oxidant is introduced, the hydrocarbon starts being oxidized, liberating heat. The liberated heat may be removed by one or more cooling means, such as cooling coils inside the reactor for example. However, it is highly preferable to remove the heat of reaction by evaporating condensible matter from the liquids in the reaction zone 14. Thus, hydrocarbon, cyclohexane for example, along with solvent, acetic acid for example, and water with minor amounts of other condensibles, formed during the oxidation process, are evaporated and condensed in the condenser 30. The condensed matter is then refluxed directly into the reaction zone 14, or more preferably is introduced to a decanter 32. In the decanter 32, the hydrocarbon with some solvent (and a minor amount of water) is separated in an upper liquid phase 34, and the water with a considerable amount of solvent, as aforementioned, and a minimal amount of hydrocarbon, is separated in a lower liquid phase 36. Non condensible gases (non-condensible in the condenser 30), such as some oxygen, nitrogen, carbon dioxide, and the like, carrying along some hydrocarbon, some solvent, some water, etc., leaves the system for further treatment and/or disposal. Nevertheless, at least partial gas recycling of non-condensible gases, sub-surface to the liquid mixture in the reaction chamber 12, may also take place, if so desired.

In the place of condenser 30 and decanter 32, a distillation column may be used, directly connected to the reaction chamber 12. With the distillation column, the individual components of the condensible matter may be separated very efficiently.

The upper phase is preferably recycled to the reaction zone 14, preferably in its totality via lines 40 and 42. However, all or part of the upper phase 34 may be removed through line 44 for further treatment. The flow rates through these lines is controlled by the first valve 43, which in turn is controlled by the controller 22, through outputs 24.

The lower phase 36, containing water with solvent, may be partially or totally recycled to the reaction chamber 12 through lines 46 and 48. It may also be removed totally or partially through line 50 for further treatment and/or disposal and or recycling to some stage of the system. The second valve 48, which controls the flow through lines 46, 48, and 50 is in turn controlled by controller 22 through inputs 24.

After the oxidation has reached a desired point of conversion of the hydrocarbon, as determined by the analytical apparatus 52, which samples the reaction zone 14 through line 52, a stream of flowable matter starts leaving the reaction zone 14 of the reaction chamber 12 through the flowable matter transfer line 74. The flow rate of the flowable matter leaving the reaction chamber 12 through line 74 is controlled by the controller 22 through outputs 24. A flow of replenishing matter enters the reaction zone 14 of the reaction chamber 12 through the liquids feeding line 16 to replenish materials consumed during the oxidation. The average flow rates of entering and exiting matter should be equal to each other volume-wise, so that the average volume of matter in the reaction chamber 12 remains substantially constant. The flowable matter leaving the reaction chamber 12 through line 74 is transferred to other stages of the reactor device 10 (not shown for purposes of clarity) for separation of the product of oxidation, such as adipic acid for example, recyclable matter, by-products, etc.

Equilibrium and a steady state are achieved as the oxidation proceeds and is controlled by controller 22. Keeping the rest of conditions substantially constant, the degree of conversion may be increased or decreased by decreasing or increasing respectively the flow rates through lines 16 and 74.

According to the present invention a steady state has to be maintained in the presence of a substantially single-phase, in addition to other requirements. One way to achieve a substantially single liquid phase is to program the controller in a manner that it takes the information from the analytical apparatus, compares it with a phase diagram, as explained below, and causes changes which will ensure a substantially single-phase liquid in the contents of the reaction chamber 12.

The variables which are important for maintenance of a substantially single liquid phase may be selected, among others, from a group consisting of temperature in the reaction zone, pressure in the reaction zone, rate of gaseous oxidant flow, water feed rate, catalyst feed rate, hydrocarbon feed rate, solvent feed rate, and a combination thereof. Under steady state conditions, and substantially constant temperature in the reaction zone, pressure in the reaction zone, rate of gaseous oxidant flow, catalyst feed rate, hydrocarbon feed rate, and solvent feed rate, the water feed rate may be used and adjusted in a manner to ensure a substantially single-phase liquid. Under the above stated conditions, there is a maximum feed rate of water, over which a second liquid phase is produced. Thus, the water feed rate has to be lower than this maximum in order to ensure the presence of just one substantially single-phase liquid.

Although phase diagrams may be multi-dimensional, ternary diagrams, which correlate three components, may be also used, if all other parameters remain constant. Also for different sets of specific parameters, respective ternary phase diagrams may be used according to the present invention. Examples of such parameters may be temperature, catalyst level, etc.

An example of such a ternary phase diagram of (Acetic Acid)/(Cyclohexane)/(Water) at 100° C., at a catalyst level of 0%, is shown in FIG. 5, wherein the one phase $R_1$ and two phase $R_2$ regions are separated by the transition line $T_0$. The one phase region $R_1$ is above the transition line $T_0$, while the two phase region $R_2$ is under the transition line $T_0$. Another example of such a ternary phase diagram of (Acetic Acid)/(Cyclohexane)/(Water) at 100° C., at a level of 4% catalyst (Cobalt(II) acetate tetrahydrate) is shown in FIG. 6, wherein the one phase $R_1$ and two phase $R_2$ regions are separated by the transition line $T_4$. The one phase region $R_1$ is above the transition line $T_4$, while the two phase region $R_2$ is under the transition line $T_4$. In the ternary phase diagram shown in FIG. 6, the water content does not include the crystalline water of cobalt(II) acetate tetrahydrate. The crystalline water is being accounted for as part of the cobalt(II) acetate tetrahydrate.

As can be seen by comparison of FIGS. 5 and 6, the presence of catalyst, cobalt(II) acetate tetrahydrate in this case, suppresses the one phase region to a certain degree. We have found that presence of adipic acid in the mixture of components does not substantially move the transition curve. Ternary diagrams for different levels of catalyst, temperature, and/or other components, which may have influence on the transition curves may be created very easily, preferably experimentally. Thermodynamic data bases and computer flow-sheet simulation programs, for example, may be used as guidelines to determine the approximate position of the transition curve, which can then be refined and defined more accurately by limited experimentation. One easy way to construct an experimental ternary diagram for a given catalyst level, temperature, etc., is for example, to select different positions in the one phase region of the theoretical diagram close to the theoretical transition curve, and start adding water until a second liquid phase is formed. This will define an experimental point on the experimental transition curve for the given catalyst level, temperature, etc. The exact compositions of the different experimental points in the diagrams shown in FIGS. 5 and 6 are listed in Tables 1 and 2, respectively. Points to the left of point 1 are omitted because the amount of cyclohexane involved is too small for most practical purposes.

In general, according to this invention, when such computer flow-sheet systems and/or diagrams and/or catalyst precipitation data, are used by the controller to operate the system and ensure that the reaction is conducted in one phase, analysis of the composition of the reaction chamber may be performed, as described above, and the flow rates of the different feeds (including recycled matter and/or operating pressure) may be changed accordingly to produce mixtures containing a substantially single-phase liquid. A similar procedure may be followed from diagrams produced at different temperatures, so that temperature manipulations may produce the desired results. Thus, for example, miscellaneous parameters may be changed to achieve the one phase desired condition, including but not limited to temperature in the reaction zone, pressure in the reaction zone, rate of gaseous oxidant flow, water feed rate, catalyst feed rate, hydrocarbon feed rate, solvent feed rate, and a combination thereof. However, if all the parameters are kept constant, then the water feed rate becomes the critical parameter for ensuring one substantially single liquid phase. The water is preferably initially provided from the decanter 32, and secondarily by addition of non-recycled water, through line 16 for example.

In order to determine the maximum amount of water allowed in the reaction zone 14, or the maximum flow rate of water entering the reaction zone 14, a different technique than the one described above may also be used. According to this technique, the upper water level monitor is utilized. As aforementioned, a sample of the contents of the reaction zone 14 of the reaction chamber 12 is transferred to the first cell 62 (FIG. 2) through line 54'. Preferably the sample fills the major part of the first cell, so that there is only a small free space above the liquid. This is important because only limited amounts of vapors may occupy the small space, thus preventing alteration of the composition of the underlying sample. The temperature of the sample in the first cell 62 is preferably maintained the same as the temperature within the reaction zone 14. Since the equilibrium steady state in the reaction zone 14 has been selected such as to contain only a substantially single liquid phase (regardless of the existence or not of solid or gaseous phases), the sample in the first cell 62 also contains a substantially single-phase liquid. If, for any reason at all, two phases are observed in the sample contained in the first cell 62, the flow rate of water to the reaction zone 14 is stepwise decreased until a sample taken from the reaction zone indicates existence of only a substantially single liquid phase. As aforementioned, the source of water is preferably the decanter 32, and only if the decanter 32 cannot provide adequate amounts of water to the reaction zone 14, a different or additional supply of water may be used.

TABLE 1

Compositions defining transition curve $T_0$ in FIG. 5
Experimental Data (0% Catalyst)

| Components | | Amount (grams) | wt % | | Amount (grams) | wt % |
|---|---|---|---|---|---|---|
| Acetic Acid | 1 | 15.105 | 75.70 | 2 | 15.586 | 77.93 |
| Water | | 3.750 | 18.79 | | 2.646 | 13.23 |
| Cyclohexane | | 1.099 | 5.51 | | 1.768 | 8.84 |
| Total | | 19.954 | | | 20.000 | |
| Acetic Acid | 3 | 15.124 | 75.27 | 4 | 12.005 | 62.18 |
| Water | | 1.762 | 8.77 | | 0.895 | 4.64 |
| Cyclohexane | | 3.207 | 15.96 | | 6.408 | 33.19 |
| Total | | 20.093 | | | 19.308 | |
| Acetic Acid | 5 | 9.859 | 48.30 | 6 | 6.550 | 32.75 |
| Water | | 0.537 | 2.63 | | 0.140 | 0.70 |
| Cyclohexane | | 10.018 | 49.08 | | 13.310 | 66.55 |
| Total | | 20.411 | | | 20.000 | |

TABLE 2

Compositions Defining Transition Curve $T_4$ in FIG. 6

| | | With 4 wt % Catalyst | | Catalyst free basis | |
|---|---|---|---|---|---|
| 1 Components | | Amount (grams) | wt % | Amount (grams) | wt % |
| Acetic Acid | | 15.198 | 72.88 | 15.198 | 75.95 |
| Cyclohexane | | 1.000 | 4.80 | 1.000 | 5.00 |
| Catalyst | | 0.844 | 4.05 | 0.000 | 0.00 |
| Water* | | 3.812 | 18.28 | 3.812 | 19.05 |
| Total | | 20.854 | | 20.010 | |
| 2 Components | | Amount | wt % | Amount | wt % |
| Acetic Acid | | 17.000 | 76.08 | 17.000 | 79.07 |
| Cyclohexane | | 2.000 | 8.95 | 2.000 | 9.30 |
| Catalyst | | 0.844 | 3.78 | 0.000 | 0.00 |
| Water* | | 2.500 | 11.19 | 2.500 | 11.63 |
| Total | | 22.344 | | 21.500 | |
| 3 Components | | Amount | wt % | Amount | wt % |
| Acetic Acid | | 14.762 | 72.56 | 14.762 | 77.08 |
| Cyclohexane | | 3.129 | 15.38 | 3.129 | 16.34 |
| Catalyst | | 0.812 | 3.99 | 0.000 | 0.00 |
| Water* | | 1.261 | 6.20 | 1.261 | 6.59 |
| Total | | 20.344 | | 19.152 | |
| 4 Components | | Amount | wt % | Amount | wt % |
| Acetic Acid | | 12.603 | 69.46 | 12.603 | 72.66 |
| Cyclohexane | | 3.843 | 21.18 | 3.843 | 22.16 |
| Catalyst | | 0.799 | 4.40 | 0.000 | 0.00 |
| Water* | | 0.899 | 4.95 | 0.899 | 5.18 |
| Total | | 18.144 | | 17.345 | |
| 5 Components | | Amount | wt % | Amount | wt % |
| Acetic Acid | | 13.606 | 67.68 | 13.606 | 70.48 |
| Cyclohexane | | 4.807 | 23.91 | 4.807 | 24.90 |
| Catalyst | | 0.798 | 3.97 | 0.000 | 0.00 |
| Water | | 0.893 | 4.44 | 0.893 | 4.63 |
| Total | | 20.104 | | 19.306 | |

TABLE 2-continued

Compositions Defining Transition Curve $T_4$ in FIG. 6

| 6 Components | With 4 wt % Catalyst | | Catalyst free basis | |
|---|---|---|---|---|
| | Amount | wt % | Amount | wt % |
| Acetic Acid | 9.799 | 47.25 | 9.799 | 49.22 |
| Cyclohexane | 10.004 | 48.24 | 10.004 | 50.25 |
| Catalyst | 0.831 | 4.01 | 0.000 | 0.00 |
| Water* | 0.106 | 0.51 | 0.106 | 0.53 |
| Total | 20.740 | | 19.909 | |

*The crystalline water of cobalt(II) acetate tetrahydrate is not included.

Nominally, in an example concerning the case of a Plant which makes about 200 million pounds of adipic acid per year, with a cyclohexane feed of about 40%, a catalyst (cobalt(II) acetate tetrahydrate) feed of about 0.5 to 1%, and a cyclohexane conversion to dibasic acids (adipic, glutaric, and succinic) of about 30%, a water feed of about 1% (in addition to the crystalline water of the cobalt(II) acetate tetrahydrate), a reaction zone pressure of 40 p.s.i.a., a 4/1 recycled gas to purged gas ratio, the water (in excess to the crystalline water of the cobalt(II) acetate tetrahydrate) in the reaction zone 14 may vary roughly from about 0.5% at 0% recycle of the lower phase in the decanter 32 to about 4% by weight at full recycle of the lower phase in the decanter 32. Water content in the reaction zone 14 rises moderately with increasing recycle of the lower phase until about 70–80% recycle, at which point water content in the reaction zone 14 starts to sharply rise with afther increases in lower phase condensate recycle. Although the water in the feed is 1%, a high enough amount of water evaporates azeotropically with cyclohexane to bring the water level in the reaction zone 14 to a level of about 0.5%, when no recycled water is used. If no water at all (recycled or not) is fed to the reaction chamber 12, the level of water (in addition to the crystalline water of the cobalt(II) acetate tetrahydrate) in the reaction zone 14 is dropped to about 0.2 to 0.3% by weight.

The first detector 66, moving up and down in the direction of arrows A may detect a second liquid phase as described earlier, and as shown in FIG. 3. Initially, since a substantially single liquid phase only exists, no peak, such as peak 76 is present in the graph of FIG. 3. At this point, a small amount of water is added to the contents of the first cell 62 through line 54". The added water may be coming either from the lower phase 36 of the decanter 32, containing considerable amounts of solvent, or as substantially pure water. It is preferable to use the lower phase 36 of the decanter 32 as source of water, since preferably this lower phase is used to adjust the water level in the reaction zone 14. The contents of the first cell 62 are maintained at the same temperature as the operation temperature in the reaction zone 14.

In sequence, the contents of the first cell 62 are thoroughly mixed with the added water, preferably by shaking the first cell 62. After each increment of water has been added and mixed, the first cell 62 is allowed to stand still for a short period of time, preferably ½ to 1 minute. The first detector 66 scans then the first cell 62, as described above, to determine whether a second liquid phase has been formed. If the first detector 66 does not detect the formation of a second liquid phase, a new small portion of water (preferably having the lower phase 36 of the decanter 32 as source) is added to the cell 62 through line 54". The contents of the first cell 62 are again thoroughly mixed with the added water, preferably by shaking the first cell 62. The first detector 66 scans again the first cell 62, as described above, to determine whether a second liquid phase has been formed. This procedure is repeated until a second liquid phase is detected by the presence of a peak, such as peak 76 in the graph of FIG. 3. At this point, the total amount of water (calculated as the % water by weight) present in the composition of the first cell 62, at the operation temperature, represents the maximum water level in the cell, and in the reaction zone 14 for all practical purposes, at which and over which the substantially single liquid phase is transformed to two liquid phases. It is obvious that the smaller the amounts of water per addition, the more accurately the maximum level may be determined. Additions of water, which increase the level of water in the first cell by 0.2% by weight per addition are preferable in many occasions. However, this incremental increase per addition may be decided based on the particular circumstances. If for example there is a relatively large gap between the maximum level of water, over which maximum level the substantially single liquid phase is transformed to two liquid phases, and the minimum level under which minimum level catalyst precipitates, then the additions may be rather large as compared to additions when said gap is relatively small. If the added water necessary for formation of a second liquid phase is less than 10% by weight of the total water contained in the cell, then the maximum level of water is being approached and water is preferably removed. Preferably, the added water necessary for formation of a second liquid phase should be controlled to be more than 20% by weight of the total water contained in the cell. This is true, not only with regard to the above referenced cell, but also to any type of technique used to determine the maximum water level necessary above which formation a second liquid phase occurs. Such techniques include, but are not limited to, computer calculations using phase diagrams, flow sheets, flow sheet simulations, energy balances, etc., well known to the art.

In order to determine the minimum level of water level in the reaction zone 14, under which minimum level catalyst precipitates, a number of techniques may be used, such as for example taking a sample from the reaction zone, and removing water incrementally by azeotropic distillation with hydrocarbon, such as cyclohexane for example, analyzing the compositions of both the sample and the reaction zone 14, and adjusting the composition of the sample to match the composition of the reaction zone 14, except for water, by adding for example to the sample miscellaneous ingredients which were removed in the process of the azeotropic distillation. The incremental water removal is continued until catalyst starts precipitating, at the operational temperature. Although this process is capable of determining the minimum level of water, under which minimum level of water catalyst precipitates, it is rather cumbersome and complicated.

According to this invention, a substantially better and faster process is one which utilizes the monitor 56, better shown in FIGS. 4A and 4B.

A sample of flowable matter taken from the reaction zone 14 is introduced into the second cell 64 of monitor 56 through line 56', in an amount to occupy most of the volume of the second cell 64 for the same reasons given earlier regarding the first cell 62.

At the operation temperature in the reaction zone 14, an adequate amount of water is present so that no precipitation of catalyst occurs, and therefore, the sample received in the second cell 64 is clear (FIG. 4A). This fact is detected by the second detector 68. If for any reason at all, catalyst has precipitated in the reaction zone 14, it is desirable to filter out the catalyst precipitate and/or increase the feed rate of the water (provided that second liquid phase formation does not occur with such increase in the feed of the water), preferably from the lower phase 36 of the decanter 32 to avoid further precipitation.

As aforementioned, it has been found that there is an unexpected precipitation of catalyst at elevated temperatures at low water levels and relatively high levels of hydrocarbon and catalyst in a single liquid phase region. It has also been found that there is a correlation between the temperature at and over which the catalyst undergoes precipitation, and the water level at and under which the catalyst undergoes precipitation. Thus, observation of temperature at which the catalyst precipitates may be used as a guide to judge whether or not the water level has to be adjusted in order to avoid catalyst precipitation.

The temperature in the second cell 64 is initially maintained the same as in the reaction zone 14. Then, it is gradually raised, preferably at a rate of about 1° C. per minute. If precipitation of catalyst occurs within a predetermined rise in temperature, the predetermined rise depending on the nature of the reaction zone, approximate composition at which the reaction is being conducted, the degree of control on the water level, and other parameters which can easily be determined in each particular case, the minimum water level under which catalyst precipitates has been approached closely, and the water feed has to be increased to avoid catalyst precipitation in case even minor spontaneous decrease in the water level or increase in temperature occurs in the reaction zone. The amount of increase is determined by also considering the maximum level of water in the reaction zone, determined by the upper water level monitor 54. Preferably the feed of water should be increased in a manner that the water level in the reaction zone 14 reaches and is maintained close to a middle level between the maximum and minimum water levels. However, under certain circumstances, it may be desirable that the water level is closer to the maximum level, or under other circumstances it may be preferable that the water level is maintained closer to the minimum level. In the case that the rise in temperature is higher than 20° C. for catalyst precipitation, no correction in water level is usually required. For in-between temperature rises, careful watch is required, and may be the water level is raised somewhat, if this raising of the water level does not come close to the maximum water level over which a second liquid phase is formed. The catalyst precipitation renders the contents of the second cell 64 at least turbid, if not substantially non-transparent, which is detected by the second detector 68 (FIG. 4B). In case of turbidity or light absorbency measurements, the catalyst precipitation may be differentiated from second liquid phase formation (and probable emulsification of one liquid phase within the other liquid phase) by the fact that the catalyst may precipitate upon raising the temperature, while a second liquid phase may be formed upon lowering the temperature. Thus, in the former case, clear contents of the cell may become turbid or absorbent upon raising the temperature, while in the latter case, clear contents of the cell may become turbid or absorbent upon lowering the temperature.

A method by which the aforementioned predetermined rise in temperature may be determined is exemplified and illustrated in FIG. 7, which represents a chart, the X axis of which is water level at or under which catalyst precipitated, and the Y axis is temperature at which the catalyst precipitated, in experiments described below and performed in a cell similar to the second cell 64. In this particular case, the amount of catalyst (cobalt(II) acetate tetrahydrate) present was 4%, the water as indicated on the X axis, and the solvent (glacial acetic acid) plus hydrocarbon (cyclohexane) constituted the rest of the composition. The crystalline water of cobalt(II) acetate tetrahydrate was not included in the amount of water indicated by the X axis. The crystalline water is accounted for as part of the cobalt(II) acetate tetrahydrate. All percentages are by weight and are based on the total of hydrocarbon plus solvent plus catalyst plus water. Line A corresponds to a ratio (by weight) of acetic acid to cyclohexane of 60:40, while line B corresponds to a ratio (by weight) of acetic acid to cyclohexane of 50:50. Although in this example only 4 components were present and were considered, products, by-products of oxidation, as well as other additional components may be present, without changing the method, for all practical purposes.

If now, for the purposes of an example, we assume that the concentration of water in the reaction zone 14 is 1% (excluding the crystalline water of the cobalt(II) acetate tetrahydrate) in a given situation, and the possible control of water level, or aximum deviation, is ±0.15%, the variation in water level may be at most from 0.85% to 1.15%. This variation of water level, corresponds to about 4° C. variation in the case of line A (acetic acid to cyclohexane weight ratio of 60:40) or to about 6.5° C. variation in the case of line B (acetic acid to cyclohexane weight ratio of 50:50). Therefore, if the operator (or the controller) obtains information from cell 64 of monitor 56 (FIGS. 4A and 4B) that it takes more than about 4° C. over the first temperature (temperature in the reaction zone 14 and of the contents of cell 64) to cause precipitation of catalyst in cell 64, in the case that the solvent to hydrocarbon ratio is about 60:40, then no addition of water in the reaction zone is necessary to ensure that the catalyst will remain in solution. Similarly, in the case of line B, where the solvent to hydrocarbon ratio is about 50:50, if the operator (or the controller) obtains information from cell 64 of monitor 56 that it takes more than about 6.5° C. over the first temperature to cause precipitation of catalyst in cell 64, then no addition of water in the reaction zone is necessary to ensure that the catalyst will remain in solution. If the temperature rises are smaller than the temperature variations mentioned above for catalyst to be precipitated, then the minimum level of water, under which catalyst is precipitated, is being approached and the water content in the reaction zone has to be increased.

Thus, the controller 22 receives respective information from the first monitor 54 and the second monitor 56, and after processing it according to a predetermined program, it causes appropriate adjustments to the water feed (recycle or fresh feed) so that the water level in the reaction zone 14 is controlled to be within a range between the desired maximum and minimum limits, as already discussed. Programming of controllers is very well known to the art.

It is possible that in some occasions, especially in the case of excessive amounts of hydrocarbon, such as cyclohexane for example, and catalyst, such as cobalt(II) acetate tetrahydrate for example, the "maximum" level of water over which a second liquid phase is formed at operation temperature, is actually lower that the "minimum" water level under which catalyst precipitates at operating temperature. In such occasions, the operation of the reaction zone is conducted at a water level lower than the maximum level of water over which a second liquid phase is formed. Otherwise, if it is desirable, either the hydrocarbon level is decreased or the catalyst level is decreased, or both, so that the level of water at which the precipitation of catalyst occurs decreases and the level at which a second liquid phase is formed increases.

In any case, when under a given set of conditions, the level of water at which or below which the catalyst precipitates is higher than the level of water at which or over which a second liquid phase is formed, there is no single liquid phase range within which a single liquid phase without precipitated catalyst exists.

The instant invention applies particularly well to cases where the hydrocarbon is cyclohexane, the solvent is acetic acid and the catalyst is cobalt(II) acetate tetrahydrate. The water level at which catalyst precipitation occurs decreases as the cyclohexane content and/or the catalyst content decrease. The water level at which a second liquid phase formation occurs increases as the cyclohexane content and/or the catalyst content decrease. Thus, with decrease in cyclohexane content and the catalyst content, the gap between the maximum level of water, over which maximum level the substantially single liquid phase is transformed to two liquid phases, and the minimum level under which minimum level catalyst precipitates, is broadened and the control of the water level adjustments is facilitated. However, at the same time the reaction rate and reactivity (reaction rate is defined as the molar oxidation of hydrocarbon per unit of time, and the reactivity defined as the reaction rate per total volume of mixture involved in the reaction) decrease. Thus, a compromise has to be made depending on the particular circumstances.

The most vulnerable region, which may greatly benefit from the teachings of the instant invention corresponds to cases wherein the cyclohexane to acetic acid ratio is in the range of about 30/70 to about 60/40. This is a very important range for the direct oxidation of cyclohexane to adipic acid in an operation temperature range of 90° to 120° C.

At a cobalt(II) acetate tetrahydrate level of about 4%, the following have been visually observed in a cell similar to the first cell 62 and second cell 64, shown in FIGS. 2 and 4A, respectively, but lacking the first detector 66 and the second detector 68, respectively. It should be noted that in all three cases (A), (B), and (C), the level of catalyst was 4% by weight, based on the sum of catalyst plus solvent (acetic acid) plus hydrocarbon (cyclohexane) plus water (excluding the crystalline water of the cobalt(II) acetate tetrahydrate, which crystalline water was taken as part of the catalyst). All levels in these cases were also calculated the same way.

(A) at 90° C.:
- (1) at a cyclohexane to acetic acid ratio of 60 to 40, a second liquid phase was formed at about and over 0.1% water level, and catalyst precipitated at about and under the same water level; therefore, there is no practical range within which a single liquid phase without precipitated catalyst exists.
- (2) at a cyclohexane to acetic acid ratio of 50 to 50, catalyst precipitation occurred at a water level of about and under 0.25%, while a second liquid phase was formed at a water level of about and over 1%; therefore the water level in a reaction zone would have to be controlled at a higher level than about 0.25% to prevent catalyst precipitation and a lower level than about 1% to prevent formation of a second liquid phase; preferably the water level should be controlled around 0.6%, which is the average between the two limits;
- (3) at a cyclohexane to acetic acid ratio of 40 to 60, no catalyst precipitation occurred even at a water level of 0%, while a second liquid phase was formed at a water level of about and over 2%; therefore the water in a reaction zone would have to be controlled at a level lower than about 2% to prevent formation of a second liquid phase without any problem of catalyst precipitation; preferably the water level should be controlled around 1%, which is the average between the 0% and 2%;
- (4) at a cyclohexane to acetic acid ratio of 30 to 70, no catalyst precipitation occurred even at a water level of 0%, while a second liquid phase was formed at a water level of about and over 3%; therefore the water in a reaction zone would have to be controlled at a level lower than about 3% to prevent formation of a second liquid phase without any problem of catalyst precipitation; preferably the water level should be controlled around 1.5%, which is the average between the 0% and 3%;

(B) at 100° C.:
- (1) at a cyclohexane to acetic acid ratio of 60 to 40, a second liquid phase was formed at about and over 0.15% water level, while catalyst precipitated at about and under 0.6% water from a two liquid phase system; therefore, there is no range within which a single liquid phase without precipitated catalyst exists);
- (2) at a cyclohexane to acetic acid ratio of 50 to 50, catalyst precipitation occurred at a water level of about and under 0.9%, while a second liquid phase was formed at a water level of about and over 1.4%; therefore the water level in a reaction zone would have to be controlled at a higher level than about 0.9% to prevent catalyst precipitation and a lower level than about 1.4% to prevent formation of a second liquid phase; preferably the water level should be controlled around 1.15%, which is the average between the two limits;
- (3) at a cyclohexane to acetic acid ratio of 40 to 60, catalyst precipitation occurred at a water level of about and under 0.1%, while a second liquid phase was formed at a water level of about and over 2.3%; therefore the water level in a reaction zone would have to be controlled at a higher level than about 0.1% to prevent catalyst precipitation and a lower level than about 2.3% to prevent formation of a second liquid phase; preferably the water level should be controlled around 1.2%, which is the average between the two limits;
- (4) at a cyclohexane to acetic acid ratio of 30 to 70, no catalyst precipitation occurred even at a water level of 0%, while a second liquid phase was formed at a water level of about and over 4.1%; therefore the water in a reaction zone would have to be controlled at a level lower than about 4.1% to prevent formation of a second liquid phase without any problem of catalyst precipitation; preferably the water level should be controlled around 2%, which is approximately the average between the 0% and 4.1%;

(C) at 1° C.:
- (1) at a cyclohexane to acetic acid ratio of 60 to 40, a second liquid phase was formed at about and over 0.2% water level, while catalyst precipitated at about and under 0.8% water from a two liquid phase system; therefore, there is no range within which a single liquid phase without precipitated catalyst exists);
- (2) at a cyclohexane to acetic acid ratio of 50 to 50, catalyst precipitation occurred at a water level of about and under 1.4%, while a second liquid phase was formed at a water level of about and over 1.9%; therefore the water level in a reaction zone would have to be controlled at a higher level than about 1.4% to prevent catalyst precipitation and a lower level than about 1.9% to prevent formation of a second liquid phase; preferably the water level should be controlled around 1.7%, which is approximately the average between the two limits;

(3) at a cyclohexane to acetic acid ratio of 40 to 60, catalyst precipitation occurred at a water level of about and under 0.8%, while a second liquid phase was formed at a water level of about and over 3.2%; therefore the water level in a reaction zone would have to be controlled at a higher level than about 0.8% to prevent catalyst precipitation and a lower level than about 3.2% to prevent formation of a second liquid phase; preferably the water level should be controlled around 2%, which is the average between the two limits;

(4) at a cyclohexane to acetic acid ratio of 30 to 70, catalyst precipitation occurred at a water level of about and under 0.2%, while a second liquid phase was formed at a water level of about and over 5.6%; therefore the water level in a reaction zone would have to be controlled at a higher level than about 0.2% to prevent catalyst precipitation and a lower level than about 5.6% to prevent formation of a second liquid phase; preferably the water level should be controlled around 2.9%, which is the average between the two limits;

(5) at a cyclohexane to acetic acid ratio of 20 to 80, no catalyst precipitation occurred even at a water level of 0%, while a second liquid phase was formed at a water level of about and over 8%; therefore the water in a reaction zone would have to be controlled at a level lower than about 8% to prevent formation of a second liquid phase without any problem of catalyst precipitation; preferably the water level should be controlled around 4%, which is the average between the 0% and 8%;

It should be understood, however, that in either case of the determination of the maximum or minimum levels of water described above, samples may be taken manually and/or examined visually to detect two liquid phase formation and/or catalyst precipitation, and the results of such determination be fed to the controller 22, or the feeds changed manually.

Going back to FIG. 2, the monitor 54 may be used for other purposes in addition to determining the maximum level of water over which a second liquid phase is formed.

As aforementioned, the monitor 54 may be used for determining the maximum level of water over which a second liquid phase is formed. However, it may also be used to predict formation of a second liquid phase under many other circumstances involving ingredients other than water.

Thus, in a different embodiment of the present invention, a sample of flowable material from the reaction zone 14 is transferred to the first cell 62, and it is maintained at the same temperature as the operation temperature of the reaction zone 14. In sequence, small amounts of hydrocarbon, cyclohexane for example, are added incrementally to the first cell 62, and mixed well with its contents. After each increment of hydrocarbon is added and mixed, the first cell 62 is allowed to stand still for a short period of time, preferably ½ to 1 minute, and the first detector scans the cell as previously described to detect whether a second liquid phase has been formed. Depending on the amount of added hydrocarbon for a second liquid phase to be formed, the operator, or the program of the controller may decide whether to make any adjustments to the feed of hydrocarbon, or even other feeds, or other conditions, in order to ensure the maintenance of a substantially single liquid phase in the reaction zone 14. Preferably, if less than 3% by weight increase in hydrocarbon concentration (based on total contents of the first cell 62) causes formation of a second liquid phase, immediate action is preferably taken to prevent possible eminent formation of a second liquid phase in the reaction zone. If, for example, the total contents of the first cell 62 are X grams, the preferable maximum addition of hydrocarbon causing formation of a second liquid phase (before action should be taken) would be 3X/(100-3)=3X/97. The type of action may be, for example, decrease of hydrocarbon, such as cyclohexane for example, in the reaction zone, decrease of water level in the reaction zone, decrease of catalyst, such as cobalt(II) acetate tetrahydrate for example, in the reaction zone, increase of solvent, such as acetic acid for example, in the reaction zone, increase of operation temperature in the reaction zone, etc.

In still a different embodiment of the present invention, a sample of flowable material from the reaction zone 14 is transferred to the first cell 62, and it is maintained at the same temperature as the operation temperature of the reaction zone 14. In sequence, small amounts of catalyst, cobalt (II) acetate tetrahydrate for example, are added incrementally to the first cell 62, and mixed well with its contents. After each increment of catalyst is added and mixed, the first cell 62 is allowed to stand still for a short period of time, preferably ½ to 1 minute, and the first detector scans the cell as previously described to detect whether a second liquid phase has been formed. Depending on the amount of added catalyst for a second liquid phase to be formed, the operator, or the program of the controller may decide whether to make any adjustments to the feed of hydrocarbon, or even other feeds, or other conditions, in order to ensure the maintenance of a substantially single liquid phase. Preferably, if less than 0.5% by weight increase in catalyst (based on total contents of the first cell 62) causes formation of a second liquid phase, immediate action is preferably taken to prevent possible eminent formation of a second liquid phase. The type of action may be, for example, decrease of hydrocarbon, such as cyclohexane for example, in the reaction zone, decrease of water level in the reaction zone, decrease of catalyst, such as cobalt(II) acetate tetrahydrate for example, in the reaction zone, increase of solvent, such as acetic acid for example, in the reaction zone, increase of operation temperature in the reaction zone, etc.

Further, in another embodiment of the present invention, a sample of flowable material from the reaction zone 14 is transferred to the first cell 62, and it is initially maintained at the same temperature as the operation temperature of the reaction zone 14. In sequence, the temperature of the contents of the first cell 62 is dropped gradually, preferably at a rate of about 1° C. per minute. If formation of a second liquid phase occurs within a predetermined decrease in temperature, preferably 5° C., immediate action is preferably taken to prevent possible eminent formation of a second liquid phase. The type of action may be, for example, decrease of hydrocarbon, such as cyclohexane for example, in the reaction zone, decrease of water level in the reaction zone, decrease of catalyst, such as cobalt(II) acetate tetrahydrate for example, in the reaction zone, increase of solvent, such as acetic acid for example, in the reaction zone, increase of operation temperature in the reaction zone, etc. In the case that the decrease in temperature is higher than 20° C. for second liquid phase formation, no correction is usually required. For in-between temperature decreases for second liquid phase formation, careful watch is required.

In another embodiment, the effect of addition of more than one of water, hydrocarbon, catalyst, and solvent, in desired quantities through line 54", may also be determined and the information used, if so desired, to be fed to the controller 22 for processing and further action. More than one cells of the type of cell 62 may be used so that the effect of additional water, hydrocarbon, catalyst, etc., on formation of a second liquid phase may be determined faster. The effect of solvent in one or more cells may be determined, if the solvent is added before or after the second liquid phase formation in the cell. Similar results may be achieved by changing the temperature up and/or down.

Of course, any combination of one or more of hydrocarbon, solvent, catalyst, water, initiator, other matter, etc. (without coming from a reaction zone) may be used in the first cell 62 of FIG. 2, at a desired temperature, for detection of a second liquid phase presence. Further, formation of a second liquid phase, at a desired temperature, by addition of any combination of one or more of hydrocarbon, solvent catalyst, water, initiator, other matter, into the first cell 62, containing a pre-existing single liquid phase mixture of components (for example hydrocarbon, solvent catalyst, water, initiator, other matter, etc.), may be observed and/or studied. In addition, any such combination may be examined for the temperature at which a second liquid phase may be formed, by varying the temperature of the first cell. Similarly, by raising the temperature from a lower temperature at which the catalyst is soluble, to a desired higher temperature, a catalyst precipitation temperature may be determined, if such a temperature exists within the range of the lower temperature to the desired higher temperature.

As aforementioned, the instant invention also pertains a method of maintaining in a reaction zone, reaction zone 14 for example, a substantially single-phase liquid mixture comprising a hydrocarbon at a first hydrocarbon level, a catalyst at a first catalyst level, a solvent at a first solvent level, and water at a first water level, the method comprising the steps of:

(a) contacting the liquid mixture, at least part of which enters the reaction zone, reaction zone 14 for example, through line 16 for example, with a gaseous oxidant entering the reaction zone 14 through line 18 for example, the temperature in the reaction zone being a first temperature, adequately high for the oxidation to proceed;

(b) taking a sample from the reaction zone 14 into a cell 62 for example;

(c) lowering the temperature of the sample to a predetermined second temperature, and if a second liquid phase is formed (as detected by the scanning detector 66 for example) at a critical temperature in the range between the first and second temperatures, either decrease in the reaction zone, reaction zone 14 for example, the first level of one component selected from a group consisting of hydrocarbon, water, catalyst, and a mixture thereof to a degree that in a new sample, a second liquid phase does not form in the range between the first and second temperatures, or increase in the reaction zone the first solvent level to a degree that in a new sample a second liquid phase does not form in the range between the first and second temperatures, or increase in the reaction zone the first temperature to a third temperature by at least the difference between the critical temperature and the second temperature, or a combination thereof.

In one example, if the first temperature in the reaction zone is 100° C., the second predetermined temperature is 95° C., and the second liquid phase formation occurred at a critical temperature of 98° C., the first temperature should be raised to be higher than 103° C. (100+98−95).

Raising the first temperature to the third temperature is undesirable in the case that catalyst precipitates in the range between the first and the third temperatures.

It should be understood that according to the present invention, any liquids or gases or off-gases may be recycled totally or partially from any section to any other section.

A preferable type of controller is a computerized controller, and more preferably a "learning computer" or a "neuro-computer", the functionality of which is known to the art, and which collects information from different places of the device (for example pressure, temperature, chemical or other analysis, etc.), stores this information along with the result (reaction rate, for example), and it is programmed to use this information in the future, along with other data if applicable, to make decisions regarding the action to be taken at each instance.

Although the miscellaneous functions are preferably controlled by a computerized controller, it is possible, according to this invention, to utilize any other type of controller or even manual controls and/or labor for controlling one or more functions.

Oxidations according to this invention, are non-destructive oxidations, wherein the oxidation product is different than carbon monoxide, carbon dioxide, and a mixture thereof, such as adipic acid for example. Of course, small amounts of these compounds may be formed along with the oxidation product, which may be one product or a mixture of products.

Examples include, but of course, are not limited to preparation of $C_5$–$C_8$ aliphatic dibasic acids from the corresponding saturated cycloaliphatic hydrocarbons, such as for example preparation of adipic acid from cyclohexane. Examples of aromatic carboxylic acids are benzoic acid, phthalic acid, isophthalic, and acid terephthalic acid, among others.

Regarding adipic acid, the preparation of which is especially suited to the methods and apparatuses of this invention, general information may be found in a plethora of U.S. Patents, among other references. These, include, but are not limited to: U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); U.S. Pat. Nos. 4,263,453; 4,331,608; 4,606,863; 4,902,827; 5,221,800; and 5,321,157.

Diacids (for example adipic acid, phthalic acid, isophthalic acid, terephthalic acid, and the like) or other suitable compounds may be reacted, according to well known to the art techniques, with a third reactant selected from a group consisting of a polyol, a polyamine, and a polyamide in a manner to form a polymer of a polyester, or a polyamide, or a (polyimide and/or polyamideimide), respectively. Preferably the polyol, the polyamine, and the polyamide are mainly a diol, a diamine, and a diamide, respectively, in order to avoid excessive cross-linking. The polymer resulting from this reaction may be spun by well known to the art techniques to form fibers.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A device comprising
a reactor comprising a reaction zone; and
a monitor for detecting formation of a second liquid phase in a mixture containing hydrocarbon, and one or more of solvent, catalyst, and water, the monitor comprising:
a cell for containing the mixture, the cell being capable of withstanding elevated pressures and temperatures;
means for maintaining a temperature and a pressure inside the cell at or near a temperature and a pressure inside the reaction zone of the reactor;
means for introducing hydrocarbon, and/or solvent, and/or catalyst, and/or water into the cell; and
an electrical conductivity detector for detecting presence or formation of a second liquid phase in the mixture within the cell upon further addition of hydrocarbon and/or solvent, and/or catalyst, and/or water into the cell.

2. A device as defined in claim 1, wherein the monitor comprises a plurality of electrical conductivity detectors within the cell.

3. A device as defined in claim 1, wherein the electrical conductivity detector is disposed in the vicinity of the bottom portion of the cell.

4. A device as defined in claim 1, wherein the electrical conductivity detector is disposed in the vicinity of the top portion of the cell.

5. A device as defined in claim 1, wherein the monitor comprises a first electrical conductivity detector disposed in the vicinity of the top of the cell, and a second electrical conductivity detector disposed in the vicinity of the bottom of the cell.

6. A device as defined in claim 1, wherein the monitor comprises a scanning conductivity detector within the cell.

7. A device as defined in claim 1, wherein the monitor is connected to a controller, which controller controls miscellaneous parameters of an oxidation reaction.

8. A device as defined in claim 2, wherein the monitor is connected to a controller, which controller controls miscellaneous parameters of an oxidation reaction.

9. A device as defined in claim 3, wherein the monitor is connected to a controller, which controller controls miscellaneous parameters of an oxidation reaction.

10. A device comprising:
a reactor comprising a reaction zone; and
a first monitor for detecting formation of a second liquid phase in a mixture, containing hydrocarbon, and one or more of solvent, catalyst, and water, the first monitor comprising:
a cell for containing the mixture, the cell being capable of withstanding elevated pressures and temperatures;
means for varying the temperature and pressure in the cell and for providing a temperature and pressure in the cell at or near the temperature and pressure of the reaction zone of the reactor;
means for introducing hydrocarbon, and/or solvent, and/or catalyst, and/or water into the cell; and
an electrical conductivity detector inside the cell for detecting presence or formation of a second liquid phase in the mixture within the cell upon further addition of hydrocarbon and/or solvent, and/or catalyst, and/or water into the cell; and
at least one additional monitor for detecting formation of a second liquid phase in the mixture.

11. A device as defined in claim 10, wherein the first monitor comprises a plurality of electrical conductivity detectors within the cell.

12. A device as defined in claim 10, wherein the electrical conductivity detector is disposed in the vicinity of the bottom portion of the cell.

13. A device as defined in claim 10, wherein the electrical conductivity detector is disposed in the vicinity of the top portion of the cell.

14. A device as defined in claim 10, wherein the first monitor comprises a first electrical conductivity detector disposed in the vicinity of the top of the cell, and a second electrical conductivity detector disposed in the vicinity of the bottom of the cell.

15. A device as define in claim 10, wherein the first monitor is connected to a controller, which controller controls miscellaneous parameters of an oxidation reaction.

16. A device comprising:
a monitor for detecting the induced formation of a second liquid phase in a mixture, the mixture including a sample, introduced into the monitor device, of the reactants and products in the reaction zone of a reactor, and containing hydrocarbon and one or more of solvent, catalyst, and water; wherein the monitor comprises:
a cell for containing the mixture, the cell being capable of withstanding elevated pressures and temperatures;
an electrical conductivity detector inside the cell for detecting the induced formation of a second liquid phase in a mixture formed upon addition, into the cell, of hydrocarbon, and/or solvent, and/or catalyst, and/or water, to the sample, already introduced into the cell, of the reactants and products in the reaction zone of the reactor;
means for introducing the sample of reactants and products into the cell, followed by incrementally and sequentially:
introducing a measured quantity of hydrocarbon, and/or solvent, and/or catalyst, and/or water into the cell;
thoroughly mixing the components of the resulting mixture in the cell;
allowing the mixture to stand for a measured amount of time, sufficient to allow the separation of two liquid phases;
engaging the electrical conductivity detector to detect the presence of a second liquid phase;
wherein the above sequence of steps is repeated until a second liquid phase is detected; and
means for maintaining the temperature and pressure in the cell at or near the temperature and pressure of the reaction zone of the reactor.

17. A device as defined in claim 16, wherein the means of thoroughly mixing the components of the resulting mixture in the cell utilizes stirring or shaking.

18. A device as defined in claim 16, further comprising means for incrementally raising or lowering the temperature of the cell by a measured number of degrees until the formation, thereby induced, of a second liquid phase is detected.

19. A device as defined in claim 16, further comprising means for promoting the separation of liquid phases that are difficult to separate into distinct portions.

20. A device as defined in claim 16, wherein the electrical conductivity detector comprises a plurality of electrical conductivity detectors.

21. A device as defined in claim 16, wherein the electrical conductivity detector is disposed in the vicinity of the bottom portion of the cell.

22. A device as defined in claim 16, wherein the electrical conductivity detector is disposed in the vicinity of the top portion of the cell.

23. A device as defined in claim 16, wherein the electrical conductivity detector comprises a first electrical conductivity detector disposed in the vicinity of the top of the cell, and a second electrical conductivity detector disposed in the vicinity of the bottom of the cell.

24. A device as defined in claim 16, wherein the electrical conductivity detector comprises at least one electrical conductivity detector adapted to scan the cell between the vicinity of the top portion of the cell and the vicinity of the bottom portion of the cell.

25. A device as defined in claim 16, wherein the monitor is connected to a controller, which controller controls miscellaneous parameters of an oxidation reaction.

\* \* \* \* \*